United States Patent [19]
Suga et al.

[11] Patent Number: 5,859,722
[45] Date of Patent: Jan. 12, 1999

[54] ELECTROCHROMIC DEVICE

[75] Inventors: Masanobu Suga; Tsuyoshi Asano; Yoshinori Nishikitani, all of Yokohama, Japan

[73] Assignee: Nippom Oil Co., Ltd, Tokyo, Japan

[21] Appl. No.: 673,075

[22] Filed: Jul. 1, 1996

[30] Foreign Application Priority Data

Jul. 4, 1995 [JP] Japan ................................. 7-168945
Mar. 25, 1996 [JP] Japan ................................. 8-068451

[51] Int. Cl.$^6$ ................................. G02F 1/157
[52] U.S. Cl. ................................. 359/265
[58] Field of Search ................................. 359/265, 275

[56] References Cited

U.S. PATENT DOCUMENTS

| | | | |
|---|---|---|---|
| 4,702,566 | 10/1987 | Tukude | 359/267 |
| 4,749,261 | 6/1988 | McLaughlin et al. | 349/16 |
| 4,990,286 | 2/1991 | Gordon | 252/518 |
| 5,387,458 | 2/1995 | Pavelka et al. | 359/361 |

*Primary Examiner*—Richard A. Rosenberger
*Attorney, Agent, or Firm*—Darby & Darby

[57] ABSTRACT

An electrochromic device having a pair of electrically conductive counter plates, an ion conductive material placed between the electrically conductive counter plates, a layer containing an electrochromic material provided in at least one of locations between the ion conductive material and the electrically conductive counter plates, at least one of the electrically conductive counter plates being a transparent electrically conductive plate having a transparent substrate and a transparent electrode disposed inside the transparent substrate, and at least one of the transparent electrically conductive plate having an ultraviolet absorbing layer containing an organic ultraviolet absorber between the transparent substrate and the transparent electrode.

35 Claims, 3 Drawing Sheets

ELECTROCHROMIC DEVICE

BACKGROUND OF THE INVENTION

This invention relates to an electrochromic device utilizing electrochromism.

An electrochromic device such as a smart window utilizing electrochromic materials is expected to be used for a wide variety of usage. However, the conventional electrochromic devices have a drawback in that they are easily deteriorated in the environment wherein ultraviolet rays are irradiated such as the outdoors.

In order to prevent the deterioration, it is suggested, for example, to provide a ultraviolet shielding layer outside a substrate constituting the smart window. However, this is not a satisfying solution in respect of appearance, wear resistance, and durability.

In an electrochromic device, usually a pair of transparent electrodes are disposed between a pair of transparent substrates, between which an electrochromic layer and an electrolyte layer are placed. It is suggested to provide an ultraviolet shielding layer inside the transparent electrodes to prevent the deterioration by ultraviolet irradiation (Japanese Laid-open Patent Application Nos. 62-148339 and 63-236016). This method does not adversely affect the abrasion resistance of the transparent substrate constituting the device. However, when the ultraviolet shielding layer is composed of metal oxides (Japanese Laid-open Patent Application No. 62-148339), near-ultraviolet area cannot be cut sufficiently, and thus the deterioration by ultraviolet rays cannot be prohibited satisfactory. Alternatively, when a dichroic layer is adopted as a ultraviolet shielding layer (Japanese Laid-open Patent Application No. 63-236016), a number of processes are required, thus being disadvantageous in cost.

SUMMARY OF THE INVENTION

It is an object of the present invention to provide an electrochromic device which has such ultraviolet resistance as to endure the use in the outdoors and which can be produced with lower cost.

According to the present invention, there is provided an electrochromic device having a pair of electrically conductive counter plates, an ion conductive material placed between the electrically conductive counter plates, a layer containing an electrochromic material provided in at least one of locations between the ion conductive material and the electrically conductive counter plates, at least one of the electrically conductive counter plates being a transparent electrically conductive plate having a transparent substrate and a transparent electrode disposed inside the transparent substrate, and at least one of said transparent electrically conductive plates having an ultraviolet absorbing layer containing an organic ultraviolet absorber between the transparent substrate and the transparent electrode.

PREFERRED EMBODIMENTS OF THE INVENTION

Figure 1:
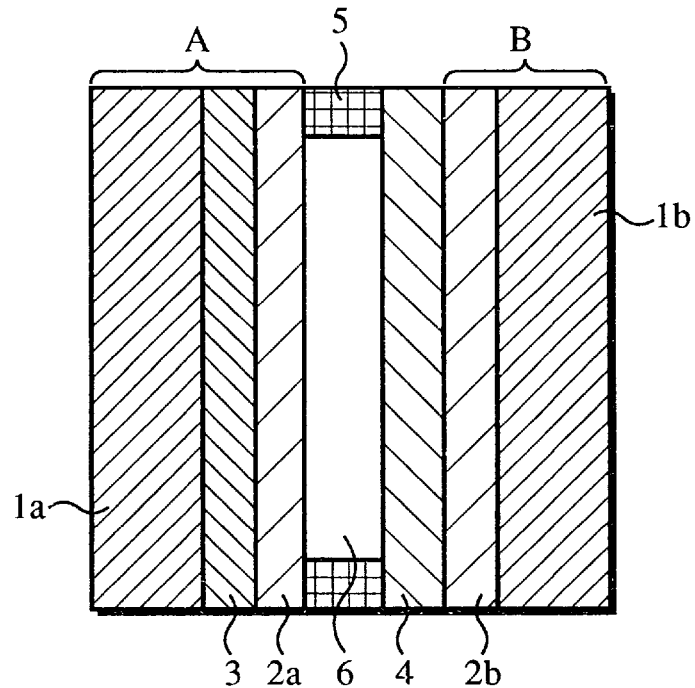
FIG. 1 is a schematic cross-sectional view illustrating the structure of the smart window of the present invention.

The present invention will be explained in further detail hereinbelow.

The electrochromic device of the present invention is basically composed of a pair of electrically conductive counter plates, an ion conductive material, a layer containing an electrochromic material, and an ultraviolet absorbing layer containing an organic ultraviolet absorber.

The electrically conductive counter plates constituting the present electrochromic device may be a plate at least of which inner surface functions as an electrode, and may specifically be (1) an electrically conductive plate which is composed in whole of a material which functions as an electrode, or (2) an electrically conductive plate having a substrate and an electrode disposed inside the substrate. However, at least one of the pair of electrically conductive counter plates should be a transparent electrically conductive plate.

When the above electrically conductive plate (1) is employed, the material which functions as an electrode may include a simple metal substance such as iron, copper, silver, aluminum, tin, lead, gold, zinc, and a variety of alloys thereof.

When the above electrically conductive plate (2) is employed, there is no particular limitation to the material of the substrate as long as the substrate has a smooth surface. Preferable material of the substrate may include, for example, various kinds of plastic materials, resins, glass, wood, and stone. There is no particular limitation to the material of the transparent substrate, and preferable material of the transparent substrate may include, for example, a colorless or colored glass, and a colorless or colored transparent resins. The resins used for the transparent substrate may include polyethylene terephthalate, polyamide, polysulfone, polyether sulfone, polyphenylene sulfide, polycarbonate, polyimide, polymethyl methacrylate, and polystyrene. For transparency in the context of the present invention, transmittance of 10% to 100% of all visible radiation all over the substrate surface suffices, and the substrate may be partially opaque. Also, the substrate has a smooth surface at ordinary temperature. The surface may be planar or curved, and may be deformed under stress.

There is no particular limitation to the electrode used in the above electrically conductive plate (2) as long as the objects of the present invention can be achieved, and the electrode preferably fulfills the requirements for transparency. The electrode disposed inside the transparent substrate of at least one of the pair of electrically conductive counter plates should be a transparent electrode. The configuration of the electrode is preferably a film or a layer. The material of the electrode may include, for example, a metal thin film made of gold, silver, chromium, copper, tungsten, or the like, and an electrically conductive film made of a metal oxide. As the metal oxide, ITO ($In_2O_3$—$SnO_2$), tin oxide, zinc oxide, or vanadium oxide may be employed.

The film thickness of the electrode is usually 100 to 5000 Å, and preferably 500 to 3000 Å. The surface resistance (resistivity) may suitably be selected depending on the usage of the electrochromic device of the present invention, but usually be 0.5 to 500 $\Omega/cm^2$, preferably 2 to 50 $\Omega/cm^2$.

There is no limitation to the method of forming the electrode, and any of known methods may be employed depending on the types of the metal and metal oxides employed for the electrode. These methods may be exemplified by a vacuum deposition method, an ion plating method, or a sputtering method. In any of these methods, the electrode may preferably be formed at the substrate temperature of usually 100° to 350° C.

The electrode may be provided partially with an opaque electrode active material for the purpose of rendering oxidation-reduction ability, electrical conductivity, and capacity for an electric double layer, and the like. When a transparent electrode is employed as an electrode, the opaque electrode active material should be provided within a range for satisfying the requirements for the transparency of the entire electrode surface. The opaque electrode active material may include, for example, a metal such as copper, silver, gold, platinum, iron, tungsten, titanium, and lithium; an organic material having oxidation-reduction ability such as polyaniline, polythiophene, polypyrrole, and phthalocyanine; carbon material such as active carbon fibers and graphite; a metal oxide such as $V_2O_5$, $WO_3$, $MnO_2$, NiO, and $Ir_2O_3$; and mixtures thereof. In order to bind these materials to the electrode, a variety of resins may be used. The electrode may be provided with the opaque electrode active material, for example, by providing a composition of active carbon fibers, graphite, an acrylic resin and the like on an ITO transparent electrode in a fine pattern such as stripes; by providing a composition of $V_2O_5$, acetylene black, butyl rubber, and the like on a thin film of gold (Au) in a meshed pattern; or the like method.

The ion conductive material used in the electrochromic device of the present invention is placed between the electrically conductive counter plates. A method for placing the ion conductive material is not particularly limited, but a method of injecting the ion conductive material into a gap formed between the electrically conductive counter plates by a vacuum injection method, a meniscus method, or a like method; or a method of forming a layer of the ion conductive material over the electrode of the electrically conductive plates by a sputtering method, a vapor-deposition method, or a like method, and then arranging the electrically conductive counter plates facing with each other, may be employed. There is no particular limitation to the ion conductive material as long as it can effect coloration, bleaching, color changes of the electrochromic material to be described later. The ion conductive material preferably has the ion conductivity of not less than $1 \times 10^{-7}$ S/cm at room temperature. The form of the ion conductive material is not particularly limited, and a liquid ion conductive material, a gelated liquid ion conductive material, and a solid ion conducive material may be employed. Among these, a solid ion conductive material is particularly preferred.

As a liquid ion conductive material, a material wherein a support electrolyte such as salts, acids, and alkalis is dissolved in a solvent may be employed.

The solvent may be of any kind as long as the support electrolyte can be dissolved therein, and preferably has polarity. Particular examples of the solvent may be water; or an organic polar solvent such as methanol, ethanol, propylene carbonate, ethylene carbonate, dimethylsulfoxide, dimethoxyethane, acetonitrile, γ-butyrolactone, sulfolane, 1,3-dioxane, N,N-dimethylformamide, 1,2-dimethoxyethane, and tetrahydrofuran. Among these, an organic polar solvent such as propylene carbonate, ethylene carbonate, dimethylsulfoxide, dimethoxyethane, acetonitrile, γ-butyrolactone, sulfolane, 1,3-dioxane, N,N-dimethylformamide, 1,2-dimethoxyethane, and tetrahydrofuran or mixtures thereof is particularly preferable.

There is no particular limitation to the salts as a support electrolyte, and inorganic ion salts such as a variety of alkali metal salts and alkaline earth metal salts, quartenary ammonium salts, cyclic quartenary ammonium salts may be employed. Specifically, alkali metal salts of lithium, sodium, or potassium such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, KSCN, KCl; quartenary ammonium salts, cyclic quartenary ammonium salts such as $(CH_3)_4NBF_4$, $(C_2H_5)_4NBF_4$, $(n-C_4H_9)_4NBF_4$, $(C_2H_5)_4NBr$, $(C_2H_5)_4NClO_4$, $(n-C_4H_9)_4NClO_4$; or mixtures thereof may be preferred.

There is no particular limitation to the acids as a support electrolyte, and inorganic acids or organic acids may be employed. Specifically, sulfuric acid, hydrochloric acid, phospholic acids, sulfonic acids, and carboxylic acids may be employed.

There is no particular limitation to the alkalis as a support electrolyte, and sodium hydroxide, potassium hydroxide, and lithium hydroxide may be employed.

As the gelated liquid ion conductive material, a material wherein a polymer and/or a gelatinizer is contained in the above-mentioned liquid ion conductive material to make the material viscous or gelated.

There is no particular limitation to the polymer, and polyacrylonitrile, carboxymethyl cellulose, polyvinyl chloride, polyethylene oxide, polyurethane, polyacrylate, polymethacrylate, polyamide, polyacrylamide, cellulose, polyester, polypropylene oxide, or nafion may be employed.

There is no particular limitation to the gelatinizer, and oxyethylene methacrylate, oxyethylene acrylate, urethane acrylate, acrylamide, or agar may be employed.

There is no particular limitation to the material of the solid ion conductive material as long as it is solid at room temperature and is electrically conductive, and polyethylene oxide, a polymer of oxyethylene methacrylate, nafion, polystyrene sulfonic acid, $Li_3N$, Na-β-$Al_2O_3$, or $Sn(HPO_4)_2 \cdot H_2O$ may be employed. Particularly, a polymeric solid electrolyte prepared with polymeric compounds obtained by polymerizing oxyalkylene methacrylate compounds or urethane acrylate compounds is preferred.

The first example of the above polymeric solid electrolyte may be a polymeric solid electrolyte prepared by solidifying a composition containing urethane acrylate represented by the formula (1) below, the above-mentioned organic polar solvent, and the above-mentioned support electrolyte (referred to as "composition A" hereinbelow):

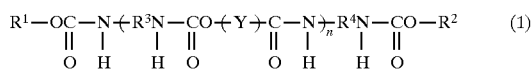

wherein $R^1$ and $R^2$ are the same or different groups, and stand for

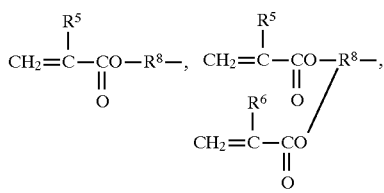

or

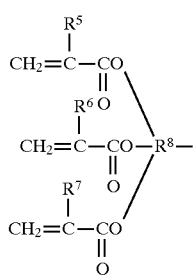

wherein $R^5$ to $R^7$ are the same or different groups and stand for a hydrogen atom or an alkyl group having 1 to 3 carbon atoms, $R^8$ stands for a divalent, trivalent, or tetravalent organic residue having 1 to 20 carbon atoms, $R^3$ and $R^4$ are the same or different groups and stand for divalent hydrocarbon residue having 1 to 20 carbon atoms, Y stands for a polyether unit, a polyester unit, a polycarbonate unit, or a combined unit thereof, and n stands for an integer of 1 to 100.

In the formula (1), the alkyl group for $R^1$ to $R^7$ may be a methyl group, an ethyl group, or a propyl group, and methyl group is particularly preferred.

In the formula (1), $R^8$ stands for a divalent, trivalent, or tetravalent organic residue having 1 to 20, preferably 2 to 8 carbon atoms. The organic residue may be a hydrocarbon residue, which may be in turn a hydrocarbon group such as an alkyltriyl group, an alkyltetralyl group, and an alkylene group represented by the formula

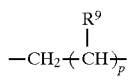

wherein $R^9$ stands for an alkyl group having 1 to 3 carbon atoms or a hydrogen atom, p stands for an integer of 0 to 6, when $2 \leq p$, $R^9$ may be the same or different.

The above-mentioned hydrocarbon residue may be a group wherein some of the hydrogen atoms in a hydrocarbon group are substituted by a group containing oxygen and hydrocarbon represented by the formula —OR (wherein R stands for a hydrocarbon group) such as an alkoxy group having 1 to 6, preferably 1 to 3 carbon atoms, and an aryloxy group having 6 to 12 carbon atoms. $R^8$ in the formula (1) may preferably be a group represented by the formula

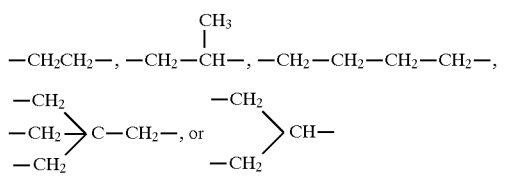

In the formula (1), $R^3$ and $R^4$ are the same or different groups, and stand for divalent hydrocarbon residue having 1 to 20, preferably 2 to 12 carbon atoms. The hydrocarbon residue may be a hydrocarbon group such as a chained divalent hydrocarbon group, a hydrocarbon group containing aromatics, and a hydrocarbon group containing alicyclics. The chained divalent hydrocarbon group may be an alkylene group represented by the formula

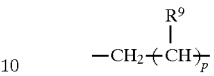

wherein $R^9$ stands for an alkyl group having 1 to 3 carbon atoms or a hydrogen atom, p stands for an integer of 0 to 6, when $2 \leq p$, $R^9$ may be the same or different.

The hydrocarbon group containing aromatics and the hydrocarbon containing alicyclics may be a hydrocarbon group represented by the formula

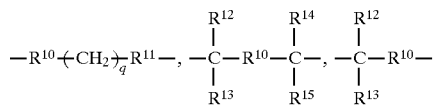

wherein $R^{10}$ and $R^{11}$ are the same or different groups and stand for a phenylene group, a substituted phenylene group (such as alkyl substituted phenylene group), or a cycloalkylene group (such as alkyl substituted cycloalkylene group), $R^{12}$ to $R^{15}$ are the same or different groups and stand for a hydrogen atom or an alkyl group having 1 to 3 carbon atoms, and q stands for an integer of 1 to 5.

$R^3$ and $R^4$ in the formula (1) may preferably be a group represented by the formula

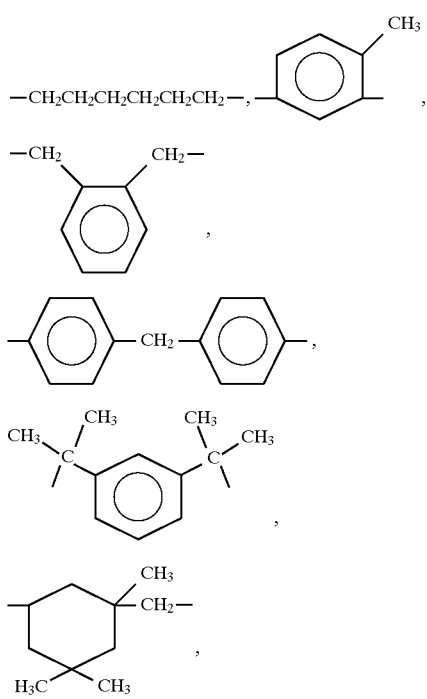

or

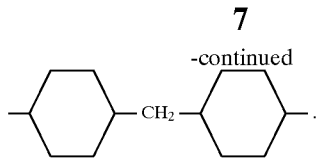

In the formula (1), Y stands for a polyether unit, a polyester unit, a polycarbonate unit, or a combined unit of these. These units may be units represented by the formulae (a), (b), and (c), respectively

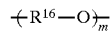 (a)

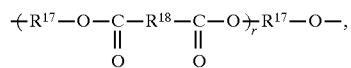 (b)

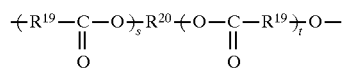

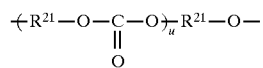 (c)

In the above formulae, $R^{16}$ to $R^{21}$ are the same or different groups, and stand for divalent hydrocarbon residue having 1 to 20, preferably 2 to 12 carbon atoms. Particularly, $R^{19}$ preferably has about 2 to 6 carbon atoms. $R^{16}$ to $R^{21}$ may preferably be a straight or branched alkylene group. Specifically, $R^{18}$ may be a methylene group, an ethylene group, a trimethylene group, a tetramethylene group, a pentamethylene group, a hexamethylene group, or a propylene group. $R^{16}$, $R^{17}$, and $R^{19}$ to $R^{21}$ may preferably be an ethylene group or a propylene group. In the above formulae, m stands for an integer of 2 to 300, preferably 10 to 200, r stands for an integer of 1 to 300, preferably 2 to 200, s stands for an integer of 1 to 200, preferably 2 to 100, t stands for an integer of 1 to 200, preferably 2 to 100, and u stands for an integer of 1 to 300, preferably 10 to 200.

In the above formulae (a), (b), and (c) representing Y, when a plurality of each unit are present, they may be the same, or different units may be copolymerized. That is, a plurality of $R^{16}$'s to $R^{21}$'s are present, $R^{16}$'s, $R^{17}$'s, $R^{18}$'s, $R^{19}$'s, $R^{20}$'s, and $R^{21}$'s may be the same or different, respectively. A particularly preferable example of the copolymer may be, in the case of the formula (a), a copolymer unit of ethylene oxide and propylene oxide.

In the formula (1), n stands for an integer of 1 to 100, preferably 1 to 50, more preferably 1 to 20.

In the formula (1), preferable number average molecular weight of the urethane acrylate represented by the formula (1) is 2500 to 30000, more preferably 3000 to 20000. If the number average molecular weight is less than 2500, the degree of cross-linking is too large and the ion conductivity may be lowered, depending on the number of functional groups for polymerization, thus being not preferred. If the number average molecular weight is more than 30000, the flexibility of the solidified material may be lowered, thus being not preferred.

The number of the functional group for polymerization in one molecule of the above-mentioned urethane acrylate is preferably 2 to 6, more preferably 2 to 4.

The urethane acrylate may preferably be a compound represented by the formula:

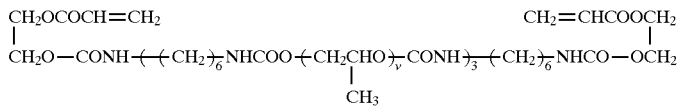

wherein v=10 to 100, preferably 30 to 80,

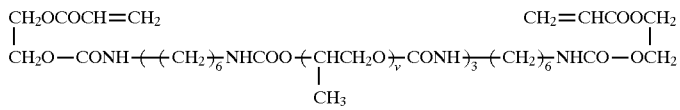

wherein v=10 to 100, preferably 30 to 80,

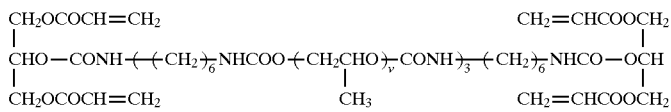

wherein v=10 to 100, preferably 30 to 80,

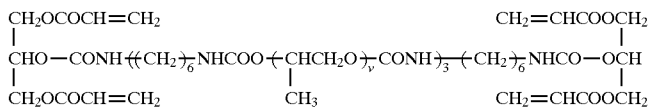
wherein v=10 to 100, preferably 30 to 80,
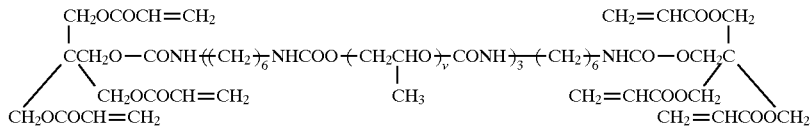
wherein v=10 to 100, preferably 30 to 80,
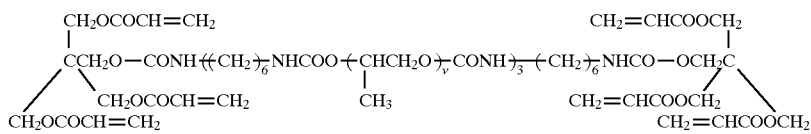
wherein v=10 to 100, preferably 30 to 80,
wherein v=10 to 100, preferably 30 to 80,
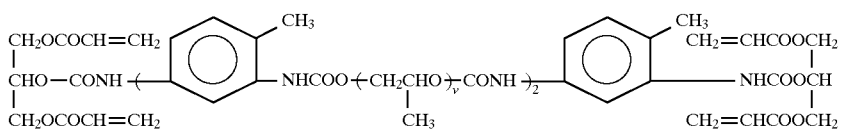
wherein v=10 to 100, preferably 30 to 80,
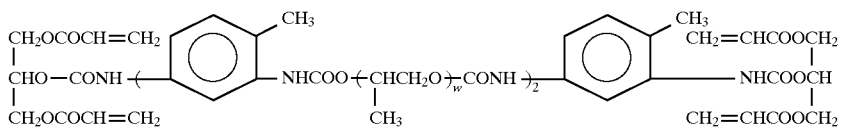
wherein w=10 to 100, preferably 30 to 80,
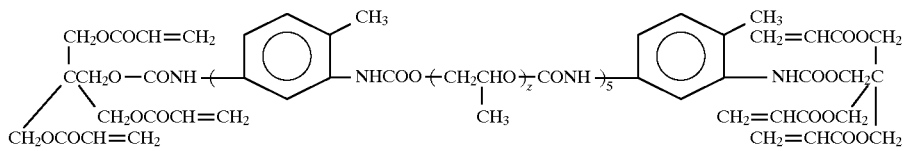
wherein z=10 to 100, preferably 20 to 70,

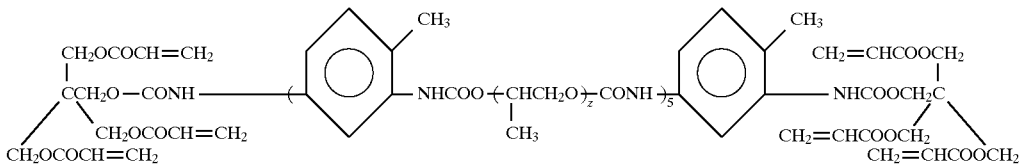

wherein z=10 to 100, preferably 20 to 70,

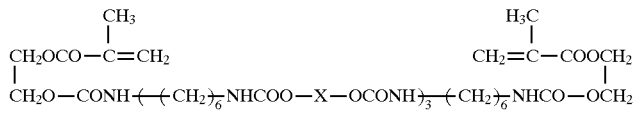

wherein X is a combined unit of ethylene oxide and propylene oxide represented by the formula

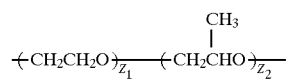

wherein the arrangement of the ethylene oxide unit and the propylene oxide unit may be block, random, or alternate, $z_1$ and $z_2$ usually stand for an integer of 1 to 100, and may be the same or different,

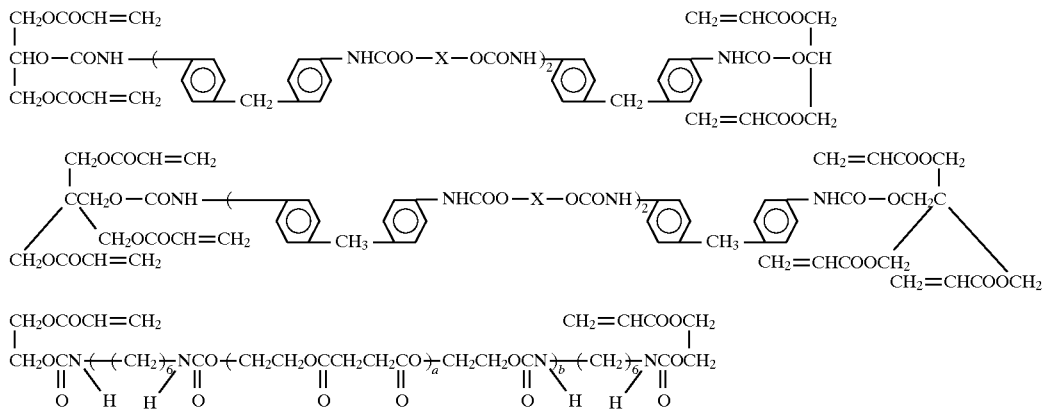

wherein a=10 to 100, preferably 30 to 80, b=1 to 10, preferably 1 to 5,

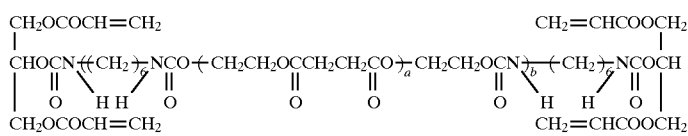

wherein a=10 to 100, preferably 30 to 80, b=1 to 10, preferably 1 to 5,

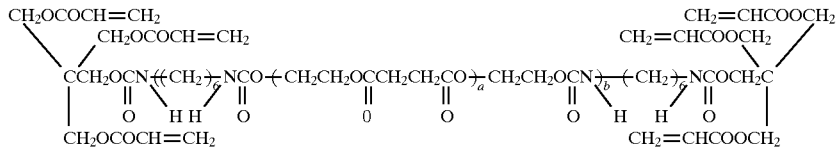
wherein a=10 to 100, preferably 30 to 80, b=1 to 10, preferably 1 to 5,
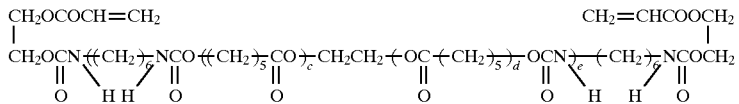
wherein c+d=5 to 50, preferably 10 to 40, e=1 to 10, preferably 1 to 5,
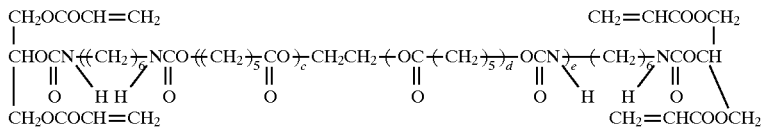
wherein c+d=5 to 50, preferably 10 to 40, e=1 to 10, preferably 1 to 5,
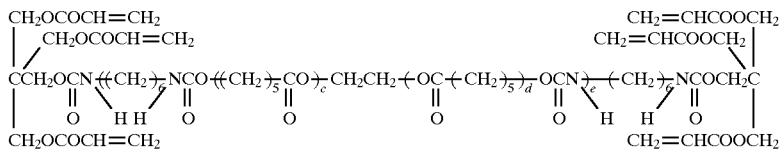
wherein c+d=5 to 50, preferably 10 to 40, e=1 to 10, preferably 1 to 5,
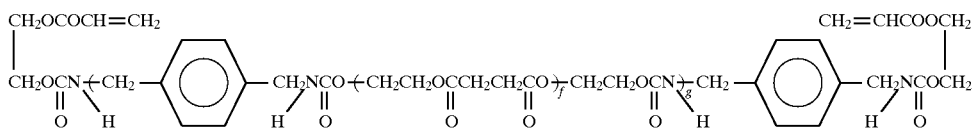
wherein f=10 to 100, preferably 30 to 80, g=1 to 10, preferably 1 to 5,
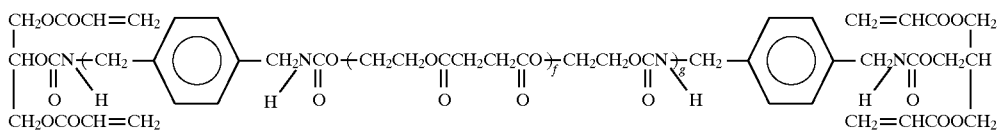
wherein f=10 to 100, preferably 30 to 80, g=1 to 10, preferably 1 to 5,

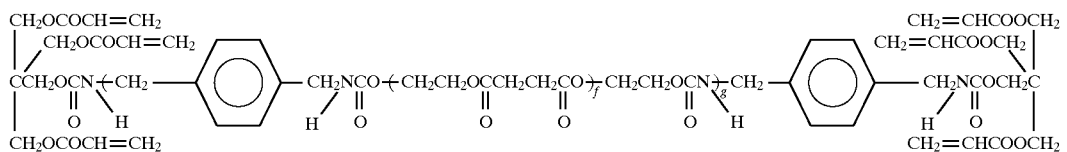
wherein f=10 to 100, preferably 30 to 80, g=1 to 10, preferably 1 to 5,
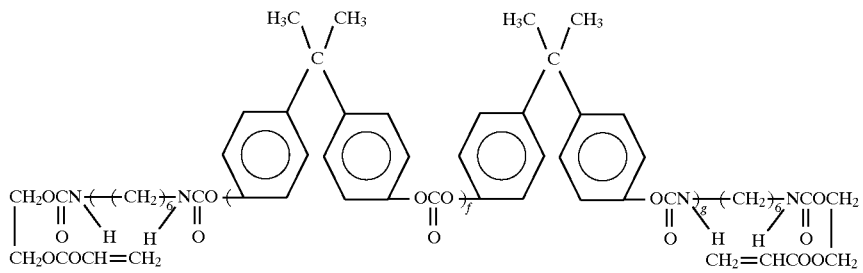
wherein f=10 to 100, preferably 30 to 80, g=1 to 10, preferably 1 to 5,
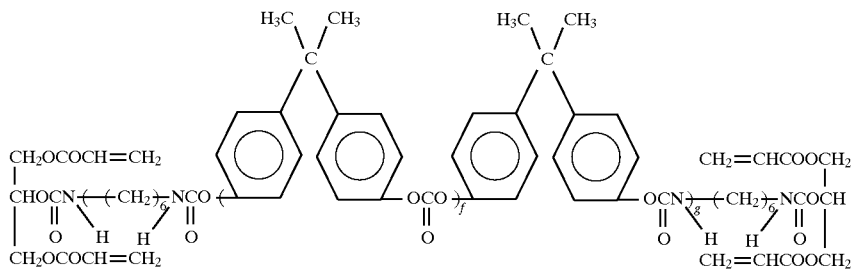
wherein f=10 to 100, preferably 30 to 80, g=1 to 10, preferably 1 to 5,
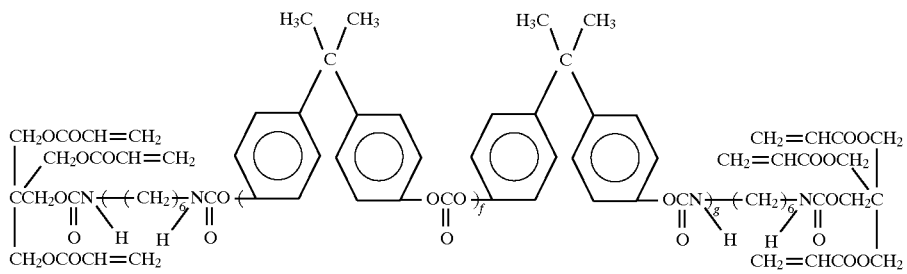
wherein f=10 to 100, preferably 30 to 80, g=1 to 10, preferably 1 to 5,
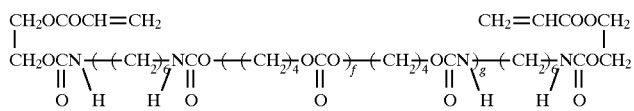

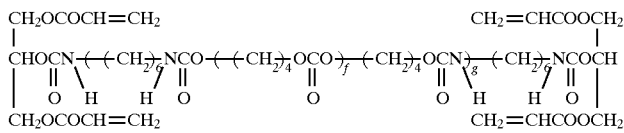

wherein f=10 to 100, preferably 30 to 80, g=1 to 10, preferably 1 to 5,

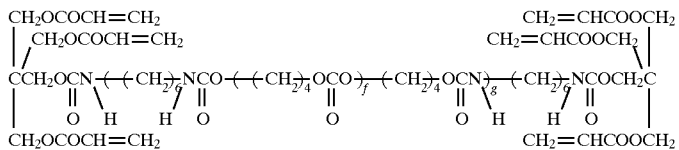

wherein f=10 to 100, preferably 30 to 80, g=1 to 10, preferably 1 to 5,

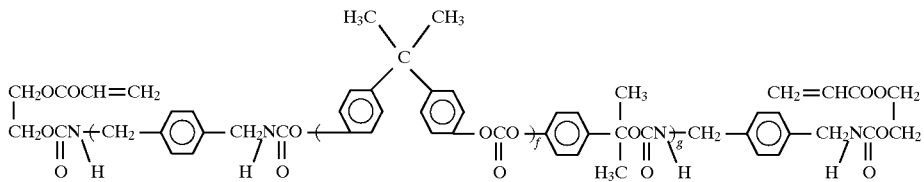

wherein f=10 to 100, preferably 30 to 80, g=1 to 10, preferably 1 to 5,

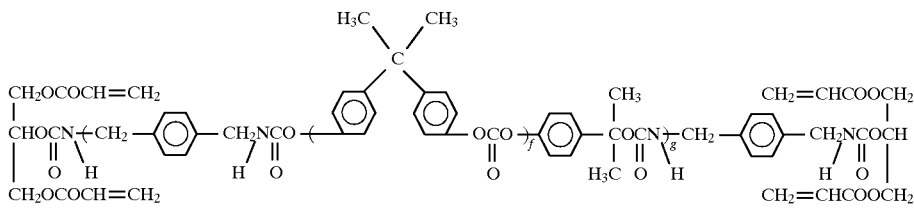

wherein f=10 to 100, preferably 30 to 80, g=1 to 10, preferably 1 to 5,

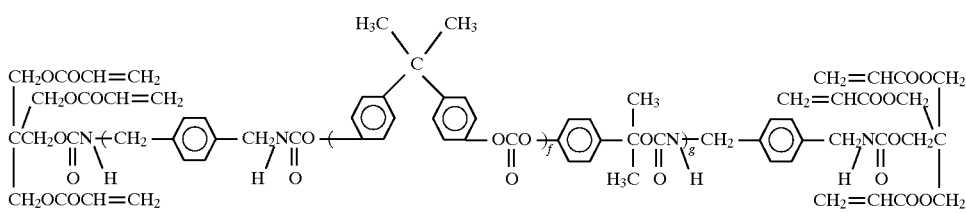

wherein f=10 to 100, preferably 30 to 80, g=1 to 10, preferably 1 to 5,

The urethane acrylate may easily be prepared by any conventional method. A preferable method may be to react polyethers, polycarbonates, or polyesters each having hydroxyl groups on both terminals, or mixtures thereof with diisocyanate, and subsequently to further react the product with acrylate having a hydroxyl group.

The number average molecular weight of the polyethers, polycarbonates, or polyesters each having hydroxyl groups on both terminals is not particularly limited, but usually 500 to 20000, preferably about 1000 to 10000.

The polyethers may be any kind as long as they derive the above-mentioned urethane acrylate, and an addition compound of polyethylene glycol, polyethylene glycol triol, polypropylene glycol, polypropylene glycol triol, polytetramethylene oxide diol, or bisphenol A to ethylene oxide or propylene oxide may be employed. Specifically, compounds represented by the formulae below may preferably be employed

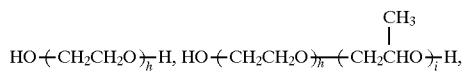

-continued

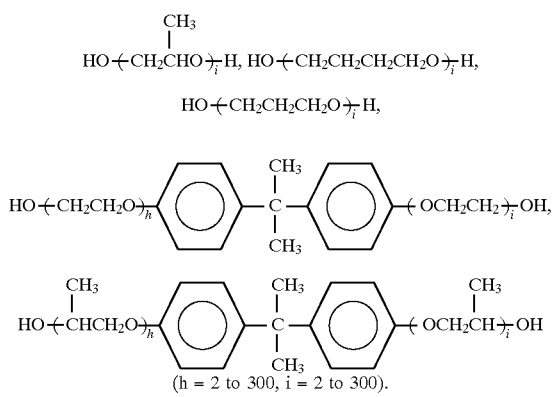

(h = 2 to 300, i = 2 to 300).

The above-mentioned polyesters and polycarbonates may be any kind as long as they derive the above-mentioned urethane acrylate, and, for example polycaprolactone diol or polycarbonate diol may be employed. Also, a dehydration product of (a) divalent carboxylic acid such as adipic acid, succinic acid, terephthalic acid, and isophthalic acid, and (b) diols such as ethylene glycol, diethylene glycol, propylene glycol, 1,4-butane diol and neopentyl glycol may be employed. Specifically, compounds represented by the formulae below may preferably be employed.

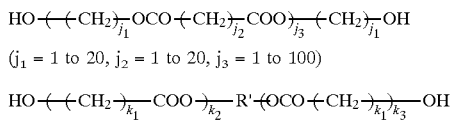

wherein R' is a hydrocarbon group such as alkylene, $k_1$=2 to 5, $k_2$=1 to 100, $k_3$=1 to 100,

wherein $l_1$=1 to 100, $l_2$=2 to 20.

The above-mentioned diisocyanate may be enumerated by, for example, tolylene diisocyanate, methylene bisphenylisocyanate, methylene bisdiethylphenylisocyanate, hexamethylene diisocyanate, methylene biscyclohexylisocyanate, α,α,α', α'-tetramethyl-1,3-xylylene diisocyanate, isophorone diisocyanate, or mixtures thereof.

The above-mentioned acrylate having a hydroxyl group may be enumerated by compounds represented by the formulae below.

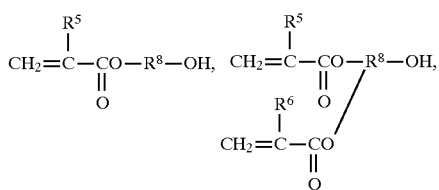

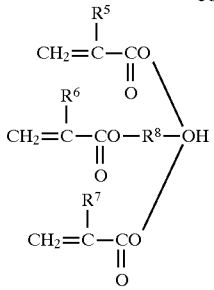

wherein $R^5$ to $R^8$ are the same as $R^5$ to $R^8$ in the formula (1).

The acrylate having a hydroxyl group may be enumerated by 2-hydroxyethyl acrylate, 2-hydroxyethyl methacrylate, 2-hydroxypropylacrylate, 4-hydroxybutyl acrylate, 2-(2-hydroxyethoxy)ethyl acrylate, 2-(2-hydroxyethoxy)ethyl methacrylate, 2-hydroxycyclohexyl acrylate, 2-hydroxycyclohexyl methacrylate, 1-hydroxycyclohexyl acrylate, 1-hydroxycyclohexyl methacrylate, 2-(2-hydroxy-1,1-dimethylethoxy)-1,1-dimethylethyl acrylate, 2-(2-hydroxy-1,1-dimethylethoxy)-1,1-dimethylethyl acrylate, 2-hydroxy-3-piperidinopropyl acrylate, 2-hydroxy-3-piperidinopropyl methacrylate, 2-hydroxy-2-phenylethyl acrylate, 2-hydroxy-2-phenylethyl methacrylate, 2-hydroxy-2-methoxypropyl acrylate, 2-hydroxy-2-methoxypropyl methacrylate, polyethylene glycol monomethacrylate, 2-hydroxy-1,3-dimethacryloyloxypropane, 2-hydroxy-1-acryloyloxy-3-methacryloyloxypropane, 2,3-diacryloylpropanol, 2,3-dimethacryloylpropanol, tetramethylolmethane triacrylate, tetramethylolmethane trimethacrylate, or mixtures thereof.

In preparing the above-mentioned urethane acrylate, the mixing ratio of polyethers, polycarbonates, or polyesters, each having hydroxyl groups on both terminals, or mixtures thereof to diisocyanate is usually 1:0.1 to 10, preferably 1:1 to 2 in molar ratio. The reaction may be effected in a solvent, preferably in a dehydrated solvent. There is no particular limitation to the solvent, and preferably the solvent does not contain active hydrogen groups. The solvent may be enumerated by, for example, aromatics such as toluene, benzen, and xylene; ketones such as methylethylketon; or dimethylsulfoxide. The above reaction is preferably effected in the presence of a catalyst such as dibutyltin dilaurate. The amount of the catalyst added is usually 0.001 to 10 mol %, preferably 0.01 to 5 mol % based on 100 mol % of diisocyanate.

The temperature and duration of the reaction may suitably be selected, but the reaction temperature is usually 0° to 150° C. preferably 20° to 120° C. and the duration of reaction is usually 10 minutes to 10 hours, preferably 20 minutes to 5 hours. There is no particular limitation to the amount of acrylate having a hydroxyl group added for the subsequent reaction, and, for example usually 1 to 10 mol, preferably 2 to 3 mol of acrylate having a hydroxyl group based on 1 mol of the reactant of the above reaction may be added. In the reaction of acrylate having a hydroxyl group, a polymerization inhibitor such as hydroquinone monomethyl ether may be added to the reactant. The reaction temperature is usually about 0° to 150° C., preferably 20° to 120° C., and the duration of the reaction is usually about 10 minutes to 10 hours, preferably 20 minutes to 5 hours. After the reaction, alcohol such as methanol may be added to the reaction mass to react the unreacted isocyanate, and the obtained reactant may be refined by a conventional method, thereby obtaining the desired urethane acrylate.

In the above composition A, the mixing ratio of the organic polar solvent is usually 100 to 1200 parts by weight, preferably 200 to 900 parts by weight based on 100 parts by weight of urethane acrylate. If the amount of the organic polar solvent added is less than 100 parts by weight, sufficient ion conductivity may not be achieved, thus not being preferred. If the amount of the organic polar solvent added is more than 1200 parts by weight, mechanical strength of the polymeric solid electrolyte to be obtained may be lowered, thus being not preferred.

The support electrolyte constituting the composition A is not particularly limited as long as the object of the present invention is not disturbed, but alkaline metal salts, quartenary ammonium salts, or alkaline earth metal salts is preferred among those listed above.

In the composition A, the mixing ratio of the support electrolyte is not particularly limited, and is preferably 0.1 to 30% by weight, more preferably 1 to 20% by weight of the total amount of the organic polar solvent.

The composition A basically contains the abovementioned urethane acrylate, the organic polar solvent, and the support electrolyte, but other components may optionally be added as required in addition to these as long as the objects of the present invention is not disturbed. For example, a cross-linking agent, a polymerization initiator, or the like may optionally be added.

The cross-linking agent may be added for the purpose of improving mechanical strength of the polymeric solid electrolyte. There is no limitation to the cross-linking agent, and the cross-linking agent having two or more functional groups, preferably acrylate compounds having two or more functional groups are preferred. Specifically, ethylene glycol dimethacrylate, diethylene glycol dimethacrylate, tetraethylene glycol dimethacrylate, ethylene glycol diacrylate, diethylene glycol diacrylate, triethylene glycol diacrylate, polyethylene glycol dimethacrylate, polyethylene glycol diacrylate, neopentyl glycol diacrylate, 1,6-hexane diol diacrylate, trimethylolpropane trimethacrylate, trimethylolpropane triacrylate, tetramethylolmethane tetraacrylate, tetramethylolmethane tetramethacrylate, or a mixture thereof may be used.

In the composition A, the mixing ratio of the cross-linking agent is preferable 0.01 to 10 mol % more preferably 0.01 to 5 mol % based on 100 mol % of the urethane acrylate.

As the above-mentioned polymerization initiator, a photopolymerization initiator or a thermal polymerization initiator may be used.

There is no particular limitation to the photopolymerization initiator, but a benzoin-type, an acetophenone-type, a benzyl ketal-type, or an acyl phosphine oxide-type photopolymerization initiator may be used. Specifically, acetophenone, benzophenone, 4-methoxybenzophenone, benzoin methyl ether, 2,2-dimethoxy-2-phenyldimethoxy-2-phenylacetophenone, benzil, benzoyl, 2-methylbenzoin, 2-hydroxy-2-methyl-1-phenyl-1-one, 1-(4-isopropylphenyl-2-hydroxy-2-methylpropane-1-one, triphenylphosphine, 2-chlorothioxanthone, 2-hydroxy-2-methyl-1-phenylpropane-1-one, 1-hydroxycyclohexylphenyl ketone, 2,2-dimethoxy-2-phenylacetophenone, 2-methyl-(4-(methylthio)phenyl)-2-morpholino-1-propanone, 2-benzyl-2-dimethylamino-1-(4-morphorinophenyl)-butane-1-one, 1-(4-(2-hydroxyethoxy) phenyl)-2-hydroxy-2-methyl-1-propane-1-one, diethoxyacetophenone, 1-(4-isopropylphenyl)-2-hydroxy-2-methylpropane-1-one, benzoin, 2,4,6-trimethylbenzoyldiphenylphosphine oxide, or a mixture thereof may be used.

There is no particular limitation to the thermal polymerization initiator, but a peroxide-containing polymerization initiator or an azo-type polymerization initiator may be used. The peroxide-containing polymerization initiator may be benzoyl peroxide, methyl ethyl peroxide, t-butyl peroxypivalate, diisopropyl peroxycarbonate, or mixtures thereof. The azo-type polymerization initiator may be 2,2'-azobis(2-isobutylonitrile), 2,2'-azobisisobutylonitrile, 2,2'-azobis(2,4-dimethylvaleronitrile), 1,1'-azobis(cyclohexane-1-carbonitrile), or mixtures thereof.

The first example of the polymeric solid electrolyte may be placed between the electrically conductive counter plates by applying or injecting the composition A to a desired location through a suitable conventional method and then solidifying the same. In this context, "solidifying" means that the polymeric or cross-linking components such as urethane acrylate are cured with the progress of polymerization or cross-linking into a substantially non-fluidizing state as a whole at ordinary temperature. In this case, urethane acrylate usually has a basic network structure (three-dimensional network structure).

The above-mentioned solidification may preferably be effected by photocuring or thermosetting the composition A to form a polymeric matrix.

The photocuring may usually be effected by using the above-mentioned photopolymerization initiator. In the composition A, the mixing ratio of the photopolymerization initiator is preferably 0.1 to 10 parts by weight, more preferably 0.1 to 5 parts by weight based on 100 parts by weight of urethane acrylate.

There is no particular limitation to the light employed for the photocuring, and far ultraviolet rays, ultraviolet rays, or visible rays may be used. The light source may be a high-pressure mercury lamp, a fluorescent lamp, or a xenon lamp. The dose is not particularly limited, and may usually be 100 to 50000 mJ/cm$^2$, preferably 1000 to 20000 mJ/cm$^2$ when a high-pressure mercury lamp is used.

The thermosetting may usually be effected by using the above-mentioned thermopolymerization initiator. In the composition A, the mixing ratio of the thermopolymerization initiator is preferably 0.1 to 10 parts by weight, more preferably 0.1 to 5 parts by weight based on 100 parts by weight of urethane acrylate.

The conditions of thermosetting reaction are selected depending on the polymerization initiator to be used, and not particularly limited. The reaction temperature is usually 0° to 130° C., preferably 20° to 80° C. The setting time is usually 30 minutes to 100 hours, preferably 1 to 40 hours.

The progress of the above-mentioned solidification may be confirmed by detecting the decline in the amount of double bonds by IR or NMR. The cross-linking structure of the cured body may be confirmed by subjecting the solidified body to extraction using a Soxhlet's extractor to confirm the residual solid, or by IR or NMR.

The second example of the above-mentioned solid electrolyte may be a polymeric solid electrolyte obtained by solidifying a composition containing a monofunctional acryloyl-modified polyalkylene oxide represented by the formula (2) below, a polyfunctional acryloyl-modified polyalkylene oxide, the above organic polar solvent, and the above support electrolyte (referred to as composition B hereinbelow).

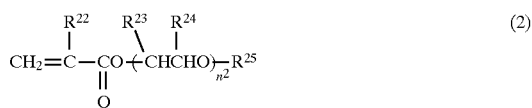

(2)

In the formula, $R^{22}$, $R^{23}$, $R^{24}$, and $R^{25}$ are the same or different groups and stand for a hydrogen atom or an alkyl group having 1 to 5 carbon atoms. The alkyl group may include a methyl group, an ethyl group, an n-propyl group, an i-propyl group, an n-butyl group, a t-butyl group, and an n-pentyl group. In particular, $R^{22}$ to $R^{24}$ preferably stand for a hydrogen atom or a methyl group, and $R^{25}$ preferably stands for a hydrogen atom, a methyl group, or an ethyl group. In the formula, $n^2$ stands for an integer of 1 or more, usually $1 \leq n^2 \leq 100$, preferably $2 \leq n^2 \leq 50$, and more preferably $2 \leq n^2 \leq 30$. If $n^2$ is 2 or more, the oxyalkylene polymer units in the formula may be the same, or different oxyalkylene units may be copolymerized. If the different oxyalkylene polymer units are copolymerized, the arrangement thereof may be random, block, or alternate.

Examples of the above-mentioned monofunctional acryloyl-modified polyalkylene oxide wherein the oxyalkylene polymer units are the same may include methoxypolyethylene glycol methacrylate, methoxypolypropylene glycol methacrylate, ethoxypolyethylene glycol methacrylate, ethoxypolypropylene glycol methacrylate, methoxypolyehylene glycol acrylate, methoxypolypropylene glycol acrylate, ethoxypolypropylene glycol acrylate, and ethoxypolypropylene glycol acrylate.

Examples of the above-mentioned monofunctional acryloyl-modified polyalkylene oxide wherein different oxyalkylene polymer units are copolymerized may include methoxypoly(ethylene/propylene) glycol methacrylate, ethoxypoly(ethylene/propylene) glycol methacrylate, methoxypoly(ethylene/propylene) glycol acrylate, and ethoxypoly(ethylene/propylene) glycol acrylate, each having 1 to 50, preferably 1 to 20 oxyethylene polymer units and 1 to 50, preferably 1 to 20 oxypropylene polymer units. These monofunctional acryloyl-modified polyalkylene oxides may be used alone or as a mixture.

There is no particular limitation to the above-mentioned polyfunctional acryloyl-modified polyalkylene oxide, but a bifunctional acryloyl-modified polyalkylene oxide represented by the formula below, or a polyfunctional acryloyl-modified polyalkylene oxide having two or more functional groups represented by the formula below (referred to as an acryloyl-modified polyalkylene oxide having two or more functional groups hereinbelow) may preferably employed:

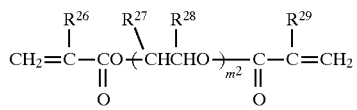

wherein $R^{26}$, $R^{27}$, $R^{28}$, and $R^{29}$ are the same or different groups and stand for a hydrogen atom or an alkyl group having 1 to 5 carbon atoms, and $m^2$ stands for an integer of 1 or more,

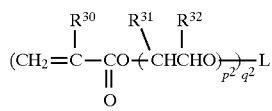

wherein $R^{30}$, $R^{31}$, and $R^{32}$ are the same or different groups and stand for a hydrogen atom or an alkyl group having 1 to 5 carbon atoms, $p^2$ stands for an integer of 1 or more, $q^2$ stands for an integer of $2 \leq p^2 \leq 4$, and L stands for a connecting group of a valency of $q^2$.

In the formula, the alkyl group for $R^{26}$, $R^{27}$, $R^{28}$, and $R^{29}$ may be a methyl group, an ethyl group, an n-propyl group, an i-propyl group, an n-butyl group, a t-butyl group, or an n-pentyl group. $R^{26}$, $R^{27}$, $R^{28}$, and $R^{29}$ preferably stand for a hydrogen atom or a methyl group.

In the formula, $m^2$ stands for an integer of 1 or more, usually $1 \leq m^2 \leq 100$, preferably $2 \leq m^2 \leq 50$, and more preferably $2 \leq m^2 \leq 30$. If $m^2$ is 2 or more, the oxyalkylene polymer units in the formula may be the same, or different oxyalkylene polymer units may be copolymerized. If the oxyalkylene polymer units are copolymerized, the arrangement may be random, block, or alternate.

Examples of the bifunctional acryloyl-modified polyalkylene oxide wherein the oxyalkylene polymer units are the same may include polyethylene glycol dimethacrylate, polypropylene glycol dimethacrylate, polyethylene glycol diacrylate, and polypropylene glycol diacrylate.

Examples of the bifunctional acryloyl-modified polyalkylene oxide wherein different oxyalkylene polymer units are copolymerized may include poly(ethylene/propylene) glycol dimethacrylate, and poly(ethylene/propylene) glycol diacrylate, each having 1 to 50, preferably 1 to 20 oxyethylene polymer units and 1 to 50, preferably 1 to 20 oxypropylene polymer units. These bifunctional acryloyl-modified polyalkylene oxides may be used alone or as a mixture.

In the formula, the alkyl group for $R^{30}$, $R^{31}$, and $R^{32}$ may be a methyl group, an ethyl group, an n-propyl group, an i-propyl group, an n-butyl group, a t-butyl group, or an n-pentyl group. $R^{30}$, $R^{31}$, and $R^{32}$ preferably stand for a hydrogen atom or a methyl group.

In the formula, $p^2$ stands for an integer of 1 or more, usually $1 \leq p^2 \leq 100$, preferably $2 \leq p^2 \leq 50$, and more preferably $2 \leq p^2 \leq 30$. If $p^2$ is 2 or more, the oxyalkylene polymer units in the formula may be the same, or different oxyalkylene polymer units may be copolymerized. If the oxyalkylene polymer units are copolymerized, the arrangement may be random, block, or alternate. Also, $q^2$ stands for an integer of $2 \leq q^2 \leq 4$.

In the formula, L stands for a coupling group of the valency of $q^2$ which couples with $q^2$ units of the acryloyl-modified polyalkylene oxides, and is usually a divalent, trivalent, or tetravalent hydrocarbon group having 1 to 30, preferably 1 to 20 carbon atoms. The divalent hydrocarbon group may include an alkylene group, an arylene group, an arylalkylene group, an alkylarylene group, and hydrocarbon groups having these groups as the basic skeleton. Specifically, a group represented by the formula below is preferred.

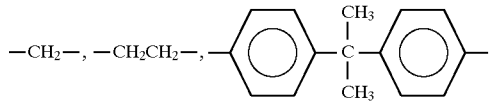

The above-mentioned trivalent hydrocarbon group may include an alkyltriyl group, an aryltriyl group, an arylalkyltriyl group, an alkylaryltriyl group, and hydrocarbon groups having these groups as the basic skeleton. Specifically, a group represented by the formula below is preferred.

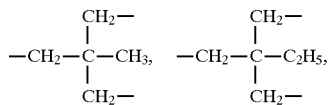

or

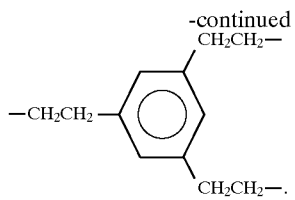

The above-mentioned tetravalent hydrocarbon group may include an alkyltetrayl group, an aryltetrayl group, an arylalkyltetrayl group, an alkylaryltetrayl group, and hydrocarbon groups having these groups as the basic skeleton. In particular, a group represented by the formula below are preferred.

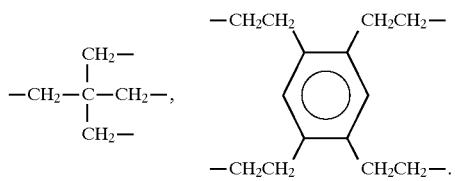

Examples of the above-mentioned acryloyl-modified polyalkylene oxide having two or more functional groups wherein the oxyalkylene polymer units are the same may include trimethylolpropane tri(polyethylene glycol acrylate), trimethylolpropane tri(polyethylene glycol methacrylate), trimethylolpropane tri(polypropylene glycol acrylate), trimethylolpropane tri(polypropylene glycol methacrylate), tetramethylolmethane tetra(polyethylene glycol acrylate), tetramethylolmethane tetra(polyethylene glycol methacrylate), tetramethylolmethane tetra(polypropylene glycol acrylate), tetramethylolmethane tetra(polypropylene glycol methacrylate), 2,2-bis(4-(acryloyloxypolyethoxy)phenyl)propane, 2,2-bis(4-(methacryloyloxypolyethoxy)phenyl)propane, 2,2-bis(4-(acryloyloxypolyisopropoxy)phenyl)propane, and 2,2-bis(4-(methacryloyloxypolyisopropoxy)phenyl)propane.

Examples of the above-mentioned acryloyl-modified polyalkylene oxide having two or more functional groups wherein different oxyalkylene polymer units are copolymerized may include trimethylolpropane tri(poly(ethylene/propylene)glycol acrylate), trimethylolpropane tri(poly(ethylene/propylene) glycol methacrylate), tetramethylolmethane tetra(poly(ethylene/propylene) glycol acrylate), and tetramethylolmethane tetra(poly(ethylene/propylene) glycol methacrylate), each having 1 to 50, preferably 1 to 20 oxyethylene polymer units and 1 to 50, preferably 1 to 20 oxyprolylene polymer units.

These acryloyl-modified polyalkylene oxides having two or more functional groups may be used alone or as a mixture.

The above divalent acryloyl-modified polyalkylene oxide and the acryloyl-modified polyalkylene oxide having two or more functional groups may be employed together.

When the above divalent acryloyl-modified polyalkylene oxide and the acryloyl-modified polyalkylene oxide having two or more functional groups are employed together, the mixing ratio of the former to the latter is usually 0.01:99.9 to 99.9:0.01, preferably 1:99 to 99:1, and more preferably 20:80 to 80:20 in weight ratio.

In the composition B, the mixing ratio of the polyfunctional acryloyl-modified polyalkylene oxide to the monofunctional acryloyl-modified polyalkylene oxide is usually 0.001 to 1:1, preferably 0.005 to 0.5:1 in weight ratio.

In the composition B, the mixing ratio of the organic polar solvent is usually 50 to 800% by weight, preferably 100 to 500% by weight of the total weight of the monofunctional acryloyl-modified polyalkylene oxide and the polyfunctional acryloyl-modified polyalkylene oxide together.

In the composition B, the mixing ratio of the support electrolyte is usually 1 to 30% by weight, preferably 3 to 20% by weight of the total weight of the monofunctional acryloyl-modified polyalkylene oxide, the polyfunctional acryloyl-modified polyalkylene oxide, and the organic polar solvent together. Further, when a plurality of kinds of support electrolytes are used, there is no particular limitation to the mixing ratio of each support electrolyte to the total amount of all the support electrolytes.

The composition B may contain other optional components as required in addition to the above components as long as the objects of the present invention is not disturbed. There is no particular limitation to the optional components, and, for example a photopolymerization initiator for photopolymerization or a thermopolymerization initiator for thermopolymerization to be described later may be contained. The photopolymerization initiator and the thermopolymerization initiator may be the compounds as listed in the first example above.

In composition B, the mixing ratio of the photopolymerization initiator, if contained, is usually 0.005 to 5 parts by weight, preferably 0.01 to 3 parts by weight based on 100 parts by weight of the monofunctional acryloyl-modified polyalkylene oxide and the polyfunctional acryloyl-modified polyalkylene oxide together.

The polymeric solid electrolyte of the second example may be placed between the electrically conductive counter plates by applying or injecting the composition B to a desired location through a suitable conventional method and then solidifying the same. In this context "solidifying" means that the polymeric or cross-linking components such as the above-mentioned monofunctional acryloyl-modified polyalkylene oxide and the polyfunctional acryloyl-modified polyalkylene oxide are cured with the progress of polymerization or cross-linking into a substantially non-fluidizing state as a whole at ordinary temperature. In this case, both the monofunctional acryloyl-modified polyalkylene oxide and the polyfunctional acryloyl-modified polyalkylene oxide usually have a basic network structure (three-dimensional network structure), respectively.

The above-mentioned solidification may preferably be effected by photopolymerizing the composition B to form a polymeric matrix, Specifically, it is preferred to prepare composition B without irradiation in advance and then solidified under irradiation. For example, the polymeric solid electrolyte may be obtained by preparing a homogeneous solution of the monofunctional acryloyl-modified polyalkylene oxide, the polyfunctional acryloyl-modified polyalkylene oxide, the organic polar solvent, and the support electrolyte, adding the photopolymerization initiator to the solution as required without irradiation (in a dark room), and irradiating the solution to solidify the same.

The conditions of the solidifying reaction by irradiation are not particularly limited, but the reaction temperature is usually $-30°$ to $80°$ C., preferably $-20°$ to $50°$ C. The light source may usually be a fluorescent lamp, an incandescent lamp, a high-pressure mercury lamp, a xenon lamp, or direct sunlight. The dose is not particular limited, but may usually be 100 to 50000 mJ/cm$^2$, preferably 1000 to 20000 mJ/cm$^2$ when a high-pressure mercury lamp is used. The duration of irradiation, i.e. the polymerization time is not particularly limited and may suitably be selected, and is usually 10 seconds to 2 hours, preferably 30 seconds to 1 hour, more preferably about 1 to 30 minutes.

The progress of the solidification may be confirmed in the same way as in the first example.

In the electrochromic device of the present invention, a layer containing an electrochromic material is provided in at least one of the locations between the ion conductive material and the electrically conductive counter plates. The electrochromic material is a material which is colored, bleached, or changed in colors by electrochemical oxidation or reduction reaction. There is no particular limitation to the electrochromic material as long as the objects of the present invention are achieved, but $Mo_2O_3$, $Ir_2O_3$, $NiO$, $V_2O_5$, $WO_3$, viologen, polythiophene, polyaniline, polypyrrole, or metalophthalocyanine may preferably be used. The above layer containing the electrochromic material may be a layer (a film) consisting of the electrochromic material alone, or a layer (a film) obtained by dispersing the electrochromic material in a matrix material, but the former is more preferable.

The thickness of the layer containing the electrochromic material is usually 10 nm to 1 μm, preferably 50 to 500 nm.

There is no particular limitation to the method of forming the layer containing the electrochromic material, and a variety of conventional methods such as vapor deposition method, ion plating method, sputtering method, electrolytic polymerization method, dip coating method, and spin coating method may be employed.

In the electrochromic device of the present invention, at least one of the electrically conductive counter plates should be a tansparent electrically conductive plate having a transparent substrate and a transparent electrode disposed inside the transparent substrate. Further, at least one of the transparent electrically conductive plate is provided with an ultraviolet absorbing layer containing an organic ultraviolet absorber between the transparent substrate and the transparent electrode. In a particular embodiment of the present invention, when the electrochromic device is composed of a pair of electrically conductive counter plates of which substrates and electrodes are all transparent, the ultraviolet absorbing layer is provided in at least one of the locations between the transparent substrate and the transparent electrodes, or in both locations. Alternatively, when the electrochromic device is composed of one transparent electrically conductive plate of which substrate and electrode are both transparent, and one non-transparent electrically conductive plate of which substrate and/or electrode is opaque, the ultraviolet absorbing layer is inevitably provided between the transparent substrate and the transparent electrode. In this case, the ultraviolet absorbing layer may be provided also between the substrate and the electrode of the non-transparent electrically conductive plate.

The ultraviolet absorbing layer contains an organic ultraviolet absorber, and may substantially be constituted by an organic ultraviolet absorber alone, or by an organic ultraviolet absorber and a basic material. The thickness of the ultraviolet absorbing layer is usually 10 nm to 100 μm, preferably 500 nm to 50 μm.

The organic ultraviolet absorber may have a benzotriazole skeleton or a benzophenone skeleton. The organic ultraviolet absorber having a benzotriazole skeleton may include 2-(2'-hydroxy-5'-methylphenyl) benzotriazole, 2-(2'-hydroxy-3', 5'-bis(α,α-dimethylbenzyl)phenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, and 3-(5-chloro-2H-benzotriazole-2-yl)-5-(1,1-dimethylethyl)-4-hydroxy-benzenepropanoic acid octyl ester. The organic ultraviolet absorber having a benzophenone skeleton may include 2,4-dihydroxybenzophenone, 2-hydroxy-4-methoxybenzophenone, 2-hydroxy-4-methoxybenzophenone-5-sulfonic acid, 2-hydroxy-4-n-octoxybenzophenone, 2,2'-dihydroxy-4,4'-dimethoxybenzophenone, 2,2',4,4'-tetrahydroxybenzophenone, and 2-hydroxy-4-methoxy-2'-carboxybenzophenone. These organic ultraviolet absorbers may be used alone or as a mixture.

In the ultraviolet absorbing layer substantially constituted by the organic ultraviolet absorber and the basic material, the organic ultraviolet absorber may be dispersed in the basic material, or the organic ultraviolet absorber and the basic material may be chemically bonded partially or substantially entirely to each other.

The organic ultraviolet absorber employed in the ultraviolet absorbing layer in which the organic ultraviolet absorber is dispersed in the basic material may be the same as the aforementioned organic ultraviolet absorber. There is no limitation to the type of the basic material, and the basic material may suitably be selected depending on the purpose and the method for manufacture of the transparent substrate. Preferred basic materials include resins, such as polyester resin, silicone resin, acrylic resin, melamine resin, phenol resin, polycarbonate resin, epoxy resin, polystyrene resin, polyether resin, polyamide resin, polyimide resin, and fluoro resin. These may be used alone or in combination. Specifically, if the ultraviolet absorbing layer is prepared without a curing process by heating, thermoplastic resins such as polystyrene resin are preferably employed as the basic material. However, if the vapor deposition method or the sputtering method is employed as a method for forming the transparent electrically conductive film, it is more preferred to use a polymer having a softening point not lower than 180° C., such as polyether sulfone or polycarbonate, since usually a high temperature is involved. If the ultraviolet absorbing layer is formed through a heating and curing process, thermosetting resins such as silicone resin or acrylic melamine resin are preferred. If the ultraviolet absorbing layer is to be produced by photocuring, acrylic resin including cross-linking agents is preferred.

In the ultraviolet absorbing layer having a configuration in which the organic ultraviolet absorber is dispersed in the basic material, the mixing ratio of the organic ultraviolet absorber to the basic material is not particularly limited, and the amount of the organic ultraviolet absorber is usually not less than 5% by weight and less than 100% by weight, preferably 10 to 80% by weight of the sum of the amounts of the organic ultraviolet absorber and the basic material. If the amount of the organic ultraviolet absorber is less than 5% by weight, sufficient ultraviolet shielding performance occasionally cannot be achieved, thus being not preferred.

In the ultraviolet absorbing layer in which the organic ultraviolet absorber and the basic material are chemically bonded partially or substantially entirely to each other, the organic ultraviolet absorber and the basic material may be chemically bonded to each other directly or via a coupling agent. The chemical bond herein means a covalent bond or an ionic bond. Examples of the covalent bond include C—C, C=C, C≡C, C—O, C—Si, C—N, C=N, C—S, C—B, C—P, and C=P, whereas examples of the ionic bond include COO—Ca—OCO and COO—Mg—OCO. Since the vapor pressure of the organic ultraviolet absorber is substantially not induced in this configuration of the ultraviolet absorbing layer, the transparent electrically conductive plate may be produced stably under reduced pressure at an elevated temperature of 300° C. or higher. Although the bonded state can be confirmed by known analytic means, it is preferred to heat the ultraviolet absorbing layer in a suitable liquid hydrocarbon, for example an aromatic solvent such as toluene, and to measure weight changes before and after the heating, as a simple index for the bonded state. If the basic material and the organic ultraviolet absorber are bonded to each other in their entirety, there is no substantial weight change before and after heating.

The method for chemically bonding the organic ultraviolet absorber to the basic material is not particularly limited, but such bonding may easily be achieved, for example by reacting or polymerizing the organic ultraviolet absorber having a group capable of reacting with a functional group contained in the basic material or a precursor of the basic material with the basic material or a precursor of the basic material. Specific examples of the method include (A) a method of mixing and bonding the organic ultraviolet absorber having introduced therein a reactive functional group such as a methacryloyl group or an alkoxy silyl group, to a coating liquid containing the basic material or the precursor thereof, in a coating or curing step, (B) a method of polymerizing an organic ultraviolet absorber having polymerizable functional groups such as an acryloyl or acryl group with a monomer of a polymerizable basic material, and (C) a method of bonding the basic material or a precursor thereof with an organic ultraviolet absorber using a coupling agent such as silane-based coupling agent. Among these, the methods (A) and (C) are preferred in that a high quality product may thereby be easily produced.

The organic ultraviolet absorber employed in the method (A) may suitably be selected depending on the basic material employed. Preferably, the compound represented by the formula below (referred to as an organic ultraviolet absorber C) may be employed.

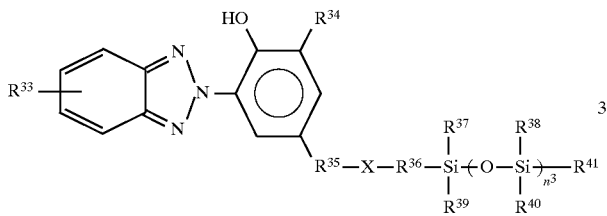

In the formula, $R^{33}$ stands for a hydrogen atom, halogen atom, or an alkyl group having 1 to 10, preferably 1 to 6 carbon atoms. Examples of the halogen atom include a fluorine atom, a chlorine atom, a bromine atom, and an iodine atom, whereas examples of the alkyl group include a methyl group, an ethyl group, a propyl group, an isopropyl group, a butyl group, a tert.-butyl group, and a cyclohexyl group.

The position of substitution of $R^{33}$ may be 4-position or 5-position of the benzotriazole skeleton in the formula. The halogen atom and the alkyl group having 1 to 10 carbon atoms may usually be substituted at 5-position.

In the formula, $R^{34}$ stands for a hydrogen atom or an alkyl group having 1 to 10, preferably 1 to 6 carbon atoms. The alkyl group may preferably include those mentioned for $R^{33}$. $R^{35}$ and $R^{36}$ in the formula are the same or different groups and stand for an alkylene group having 1 to 6, preferably 1 to 3 carbon atoms. The alkylene group may include a methylene group, a ethylene group, and a propylene group. $R^{37}$ to $R^{41}$ in the formula are the same or different groups, and stand for an alkyl group having 1 to 10, preferably 1 to 6 carbon atoms, an alkoxy group having 1 to 10, preferably 1 to 6 carbon atoms, an aryl group having 6 to 10, preferably 6 to 8 carbon atoms, a hydroxyl group, or a hydrogen atom. The alkyl group may preferably include those mentioned for $R^{33}$. The alkoxyl group may preferably include a methoxy group, an ethoxy group, an isopropoxy group, a propoxy group, a butoxy group, and a tert.-butoxy group. The aryl group may preferably include a phenyl group and a xylyl group. X denotes an amido bond (CONH), an urethane bond (OCONH), or an ester bond (COO). n stands for an integer of $n^3 \geq 0$, preferably $0 \leq n^3 \leq 20$.

The organic ultraviolet absorber C represented by the above formula may be enumerated by 3-(5-methyl-2-H-benzotriazole-2-yl)-5-methyl-4-hydroxy-N-(2-(trimethoxysilyl)ethyl)-benzene propanamide, 3-(5-ethyl-2H-benzotriazole-2-yl)-4-hydroxy-N-(2-(1,1,3,3-tetramethyldisiloxy)ethyl)-benzene propanamide, 3-(2H-benzotriazole-2-yl)-4-hydroxybenzene ethyl-N-(3-trimethoxysilyl)propyl)carbamate, 3-(5-chloro-2H-benzotriazole-2-yl)-4-hydroxybenzene propyl-N-(2-nonaphenyltetrasiloxy)ethyl)carbamate, 3-(5-chloro-2H-benzotriazole-2-yl)-5-(1,1-dimethylethyl)-4-hydroxy-N-(3-(triethoxysilyl)propyl)-benzene propanamide, 3-(5-chloro-2H-benzotriazole-2yl)-5-(1,1-dimethylethyl)-4-hydroxy-N-(3-(triethoxysilyl)propyl)-benzene propanamide, 3-(5-chloro-2H-benzotriazole-2-yl)-5-(1,1-dimethylethyl)-4-hydroxy-N-(3-henicosamethyldecasiloxy) propyl-benzene propanamide, 3-(2H-benzotriazole-2-yl)-4-hydroxy-N-(2-(1,1-dimethyl-trimethoxydisiloxy)ethyl)-benzene propaneamide, 3-(triethoxysilyl)propyl-3-(5chloro-2H-benzotriazole-2-yl)-5-(1,1-dimethylethyl)-4-hydroxy-benzene propanate, 3-(1,1,3,3,5,5,5-heptamethyltrisiloxy)propyl-3-(5-chloro-2H-benzotriazole-2-yl)-5-(1,1-dimethylethyl)-4-hydroxy-benzene propanate, and 3-(diethoxymethylsilyl)propyl-3-(2H-benzotriazole-2-yl)-5-(1,1-dimethylethyl)-4-hydroxy-benzene propanate.

The organic ultraviolet absorber C may easily be prepared by a conventional method, for example by bonding a variety of benzotriazoles with a variety of silanes. Specifically, the organic ultraviolet absorber C having a structure in which benzotriazoles and silanes are coupled to each other via an amido bond may be prepared by coupling the benzotriazoles having a carboxyl group with silanes having an amino group. The organic ultraviolet absorber C having a structure in which benzotriazoles and silanes are coupled to each other via an urethane bond may be prepared by coupling the benzotriazoles having a hydroxyl group with silanes having an isocyanate group. Further, the organic ultraviolet absorber C having a structure in which benzotriazoles and silanes are coupled to each other via an ester bond may be prepared by adding a compound having a benzotriazole and an an unsaturated hydrocarbon bonded to each other by an ester bond to a silane having a hydrosilyl group.

The precursor of the basic material to be bonded to the organic ultraviolet absorber C may be enumerated by reactive monomers such as methacrylic monomers or alkoxy silanes; and reactive oligomers such as acrylic oligomers and silicone oligomers.

There is no limitation to the basic material to be bonded to the organic ultraviolet absorber C, and any of those specified above as the basic material for constituting the ultraviolet absorbing layer in which the organic ultraviolet absorber is dispersed in the basic material may be used.

The combination of the organic ultraviolet absorber C with the precursor of the basic material produced by the method (A) may further be mixed with other basic materials. In this case, there is no limitation to the other basic materials employed, and those basic materials bonded to the organic ultraviolet absorber C may be used.

The preferred combination of the organic ultraviolet absorber with the coupling agent in the above method (C) may be enumerated by a combination (C-a) of the organic ultraviolet absorber of carboxylic acids and a coupling agent of aminosilanes, a combination (C-b) of an organic ultraviolet absorber of alcohols and a coupling agent of isocyanate silanes, and a combination (C-c) of an organic ultraviolet absorber of esters with a coupling agent of silanes.

The organic ultraviolet absorber of carboxylic acid in the combination (C-a) may be enumerated by carboxylic acids represented by the formula:

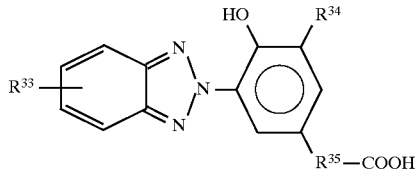

wherein $R^{33}$, $R^{34}$, and $R^{35}$ have the same meaning as those for the organic ultraviolet absorber C.

The carboxylic acids represented by the above formula may be enumerated by 3-(5-chloro-2H-benzotriazole-2-yl)-5-(1,1-dimethylethyl)-4-hydroxy-benzene propanoic acid, 3-(2H-benzotriazole-2-yl)-4-hydroxy-benzene ethanoic acid, and 3-(5-methyl-2H-benzotriazole-2-yl)-5-(1-methylethyl)-4-hydroxy-benzene propanoic acid.

The coupling agent of aminosilanes in the combination (C-a) may be enumerated by aminosilanes represented by the formula:

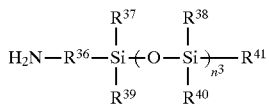

wherein $R^{36}$ to $R^{41}$ and $n^3$ have the same meaning as those of the above organic ultraviolet absorber C.

The aminosilanes represented by the above formula may include 3-aminopropyltriethoxysilane, 3-aminopropyldiisopropylethoxysilane, 3-aminopropylmethyldiethoxysilane, 3-aminopropylpolydimethylsiloxane, N-(2-aminoethyl)-3-aminopropyltrimethoxysilane, and 3-aminopropyltris (methoxyethoxyethoxy)silane.

The organic ultraviolet absorber of alcohols in the combination (C-b) may be enumerated by alcohols represented by the formula:

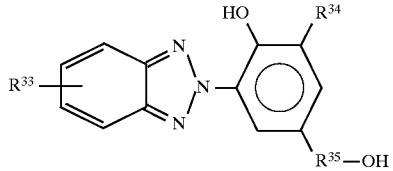

wherein $R^{33}$, $R^{34}$, and $R^{35}$ have the same meaning as those of the above organic ultraviolet absorber C.

Examples of the alcohols represented by the above formula may include 3-(5-chloro-2H-benzotriazole-2yl)-5-(1,1-dimethylethyl)-4-hydroxy-benzene propanol, 3-(2H-benzotriazole-2-yl)-4-hydroxy-benzene ethanol, and 3-(5-methyl-2H-benzotriazole-2-yl)-5-(1-methylethyl)-4-hydroxy-benzene propanol.

The coupling agent of isocyanate silanes in the combination (C-b) may be enumerated by isocyanate silanes represented by the formula:

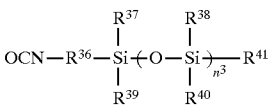

wherein $R^{36}$ to $R^{41}$ and $n^3$ have the same meaning as those of the above organic ultraviolet absorber C.

Examples of the isocyanate silanes represented by the above formula may include 3-isocyanatopropyltriethoxysilane, 3-isocyanatopropylmethoxydimethylsilane, and 2-isocyanatoethylpolydimethylsiloxane.

The organic ultraviolet absorber of esters in the combination (C-c) may be enumerated by esters represented by the formula:

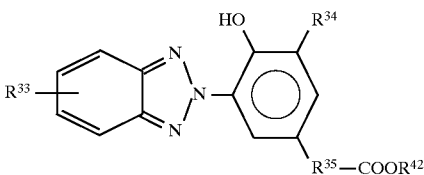

wherein $R^{33}$, $R^{34}$, and $R^{35}$ have the same meaning as those of the above organic ultraviolet absorber C, $R^{42}$ stands for a hydrocarbon group having unsaturated double bond and 1 to 10 carbon atoms, and specifically, $R^{42}$ becomes identical with $R^{36}$ of the organic ultraviolet absorber C by addition reaction.

Examples of the esters represented by the above formula may include 2-propenyl 3-(5-chloro-2H-benzotriazole-2-yl)-5(1,1-dimethylethyl)-4-hydroxy-benzene propanoate, vinyl 3-(2H-benzotriazole-2-yl)-4-hydroxy-benzene ethanoate, and 3-methyl-3-butenyl 3-(5-methyl-2H-benzotriazole-2-yl)-5-(1-methylethyl)-4-hydroxy-benzene propanoate.

The coupling agent of silanes in the combination (C-c) may be enumerated by silanes represented by the formula:

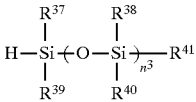

wherein $R^{37}$ to $R^{41}$ and $n^3$ have the same meaning as those of the above organic ultraviolet absorber C.

Examples of the silanes represented by the above formula may include triethoxysilane, diisopropylethoxysilane, methyldiethoxysilane, and poly(methylhydrosiloxane).

The basic material and the precursors thereof employed in the above method (A) may be used as the basic materials and the precursors thereof enumerated in the above method (C).

There is no limitation to the method for forming the ultraviolet absorbing layer, and any of conventional methods may be selectively employed. Specifically, the ultraviolet absorbing layer containing the organic ultraviolet absorber may be produced by coating a solution of the organic ultraviolet absorber; a solution containing the organic ultraviolet absorber and the basic material or the precursor thereof or a fused mass thereof; or a solution containing the organic ultraviolet absorber, the basic material or the precursor thereof, and a coupling agent, or a fused mass thereof, and by performing necessary processing operations after such coating depending on the material employed. The coating methods may usually be selected from spin coating, spray coating, cast coating, and blade coating depending on the purpose. The processing operation after the coating usually consist in curing by heating. However, curing by allowing to stand at room temperature and/or by light irradiation may be suitably employed depending on the properties of the resin. The method of heat curing includes heating on a hot plate or in an oven usually at a temperature of 50° to 400° C. The method of photocuring includes irradiation by a high-pressure mercury lamp, a low-pressure mercury lamp, a fluorescent lamp, or a xenon lamp with ultraviolet rays or visible light usually for 5 seconds to 24 hours.

The electrochromic device of the present invention may be provided with an overcoating layer between the ultraviolet absorbing layer and the transparent electrode for the purpose of protecting the ultraviolet absorbing layer upon forming the transparent electrode. The overcoating layer may be formed of a resin, which is preferably stable and smooth upon forming the transparent electrode and is capable of maintaining the transparency.

The overcoating layer is usually formed of a material having superior thermal resistance. Examples of the resin may include polyimide, polyamide, polycarbonate, polyallylate, polyether sulfone, melamine resin, phenol resin, epoxy resin, silicone resin such as silicone varnish, and urea resin. Among these, the silicone resin such as silicon varnish is the most preferred. These resins may be used alone or in combination. These resins may also be used with glass fillers or inorganic powders. The inorganic powders may be fine powders of $ZnO$, $TiO_2$, $CeO_2$, or silica.

There is no limitation to the method of forming the overcoating layer, and any conventional method may suitably be selected. Usually, the overcoating layer may be formed by coating a solution of a resin for forming the overcoating layer or a solution of a precursor for the resin in a desired location. After the coating, necessary processing operations depending on the properties of the respective resins are performed, thereby obtaining the overcoating layer. The overcoating layer may also be formed by applying a film formed of the above resins in a desired location.

Specifically, the overcoating layer may be formed, for example when a silicone varnish is employed, by adding a catalyst such as dibutyltin dilaurate to the silicone varnish, coating the mixture, and heat curing the coating at 100° to 200° C. for 5 minutes to 2 hours to give an overcoating layer of 1 to 20 $\mu$m thick. When an acrylic melamine resin precursor is employed, the overcoating layer may be formed by effecting the heat curing at 130° to 190° C. for 5 minutes to 2 hours after the coating to give an overcoating layer of 10 to 100 $\mu$m thick. If a photocuring type acrylic resin precursor is employed, the overcoating layer may be formed by irradiating the coated product with light of a high-pressure mercury lamp to give an overcoating layer of 1 to 10 $\mu$m thick within five minutes, The above resins may be coated by a conventional method such as spin coating, spray coating, cast coating, blade coating, or dip coating.

The electrochromic device of the present invention is constructed with a pair of electrically conductive counter plates at least of one of which is a transparent electrically conductive plate, an ion conductive material, a layer containing electrochromic material, and an ultraviolet absorbing layer. As specific embodiments of the electrochromic device of the present invention, embodiments of smart windows of the present invention will be explained in more detail with reference to the drawings.

The simplest configuration of the smart window of the present invention is, for example as shown in FIG. 1, wherein a transparent electrically conductive plate A having a transparent substrate 1a, a transparent electrode 2a positioned inside the transparent substrate 1a, and an organic ultraviolet absorbing layer 3 formed therebetween, and a transparent electrically conductive plate B having a transparent substrate 1b and a transparent electrode 2b positioned inside the transparent substrate 1b, are arranged in a facing relation with each other. An electrochromic layer 4 is formed inside the transparent electrode 2b of the transparent electrically conductive plate B, and an ion conductive material 6 is located between the transparent conductive plate A and the transparent electrically conductive plate B provided with the electrochromic layer 4, with the layer of the ion conductive material 6 being sealed with a sealing agent 5.

Figure 2:
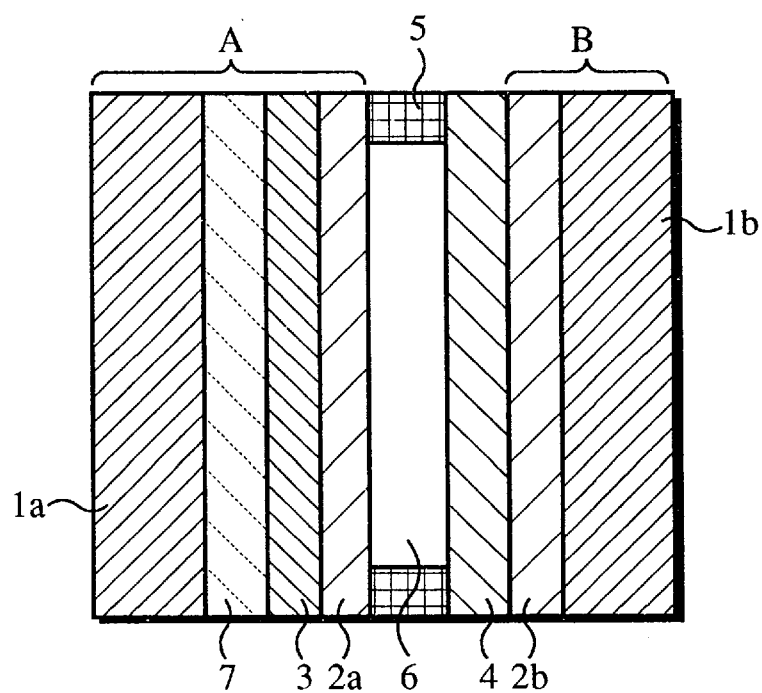
FIG. 2 is a schematic cross-sectional view illustrating the structure of another smart window of the present invention.

As shown in FIG. 2, one or more intermediate layers 7 may be provided between the transparent substrate 1a and the organic ultraviolet absorbing layer 3. There is no limitation to the function of the intermediate layer 7. For example, a far ultraviolet absorbing layer containing an inorganic oxide such as $ZnO$, $CeO_2$, or $TiO_2$ may be provided for prohibiting deterioration of the organic ultraviolet absorber since some kinds of organic ultraviolet absorber may be deteriorated by far ultraviolet rays. An intermediate layer 7 containing a silane coupling agent or a surface active agent may also be provided for the purpose of improving the adhesion between the organic ultraviolet absorbing layer 3 and the transparent substrate 1a. In FIG. 2, the members referred to by the same reference numerals as in FIG. 1 are the same members and will not be explained here.

Figure 3:
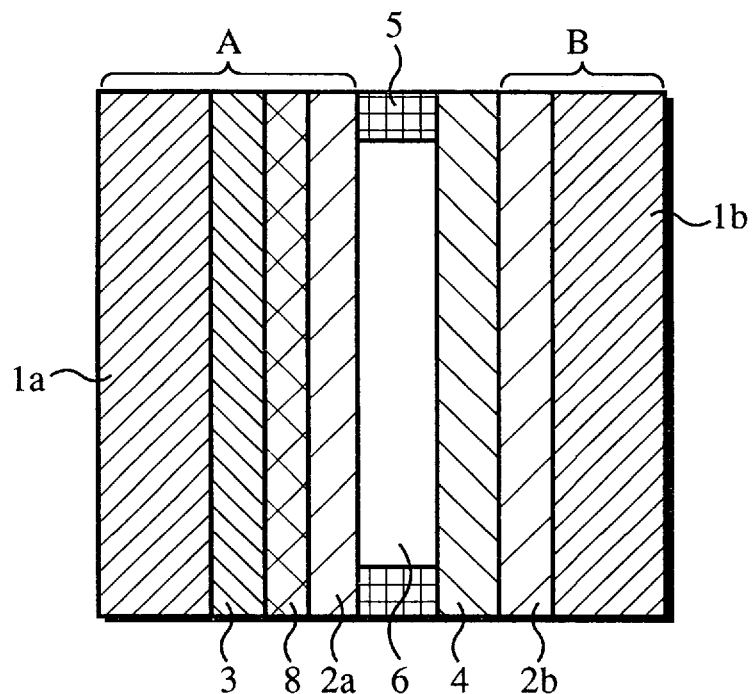
FIG. 3 is a schematic cross-sectional view illustrating the structure of still another smart window of the present invention.

As shown in FIG. 3, an overcoating layer 8 may be provided between the organic ultraviolet absorbing layer 3 and the transparent electrode 2a. There is no limitation to the function of the overcoating layer 8, and the overcoating layer 8 may be provided for the purpose of protecting the organic ultraviolet absorbing layer 3 upon forming the transparent electrode 2a, or electrically insulating the transparent electrode 2a and the organic ultraviolet absorbing layer 3 after the assembling of the smart window. In FIG. 3, the members referred to by the same reference numerals as in FIG. 1 are the same members and will not be explained here.

Figure 4:
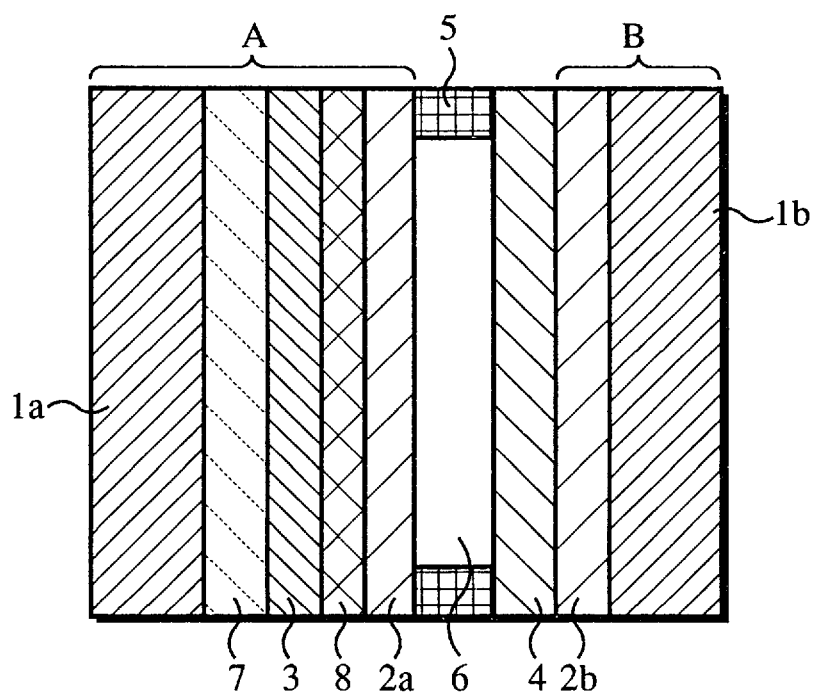
FIG. 4 is a schematic cross-sectional view illustrating the structure of yet another smart window of the present invention.

As shown in FIG. 4, an intermediate layer 7 may be provided between the transparent electrode 1a and the organic ultraviolet absorbing layer 3, and an overcoating layer 8 may also be provided between the organic ultraviolet absorbing layer 3 and the transparent electrode 2a. In FIG. 4, the members referred to by the same reference numerals as in FIGS. 1 to 3 are the same members and will not be explained here.

Figure 5:
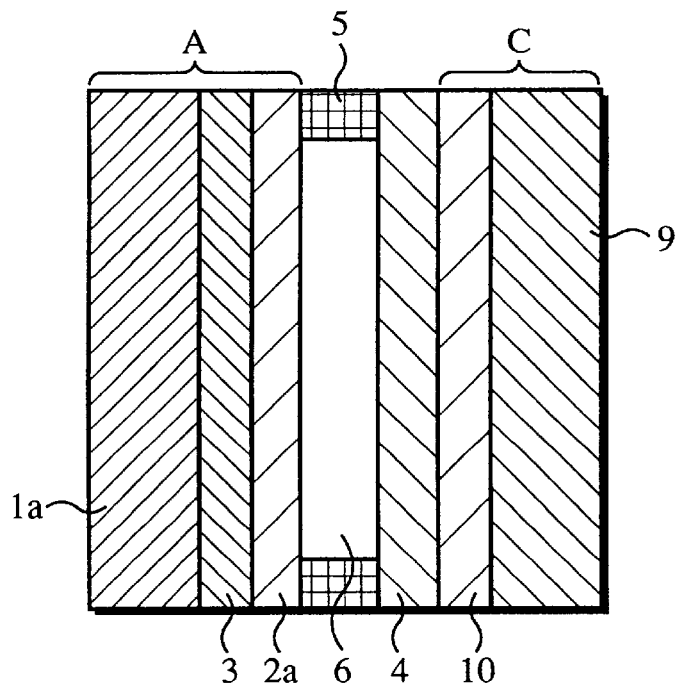
FIG. 5 is a schematic cross-sectional view illustrating the structure of still another smart window of the present invention.

As shown in FIG. 5, an electrically conductive plate C having an opaque substrate 9 and an opaque electrode 10 may be provided in place of the transparent electrically conductive plate B in FIGS. 1 to 4. In FIG. 5, the members referred to by the same reference numerals as in FIG. 1 are the same members and will not be explained here.

There is no limitation to the method of forming the respective films and layers constituting the electrochromic device such as a smart window of the present invention, and each film and layer may be formed in order according to the above methods. For example, in the case of the smart window having the structure as shown in FIG. 1, a transparent electrically conductive plate A is obtained by forming in order an organic ultraviolet absorbing layer 3 and a transparent electrode 2a on a transparent substrate 1a according to the above methods. Next, transparent electrically conductive plate 1b is obtained by forming in order a transparent electrode 2b and an electrochromic layer 4 on another transparent substrate 1b according to the above methods. These transparent electrically conductive plates 1a and 1b are arranged in a facing relation to each other with a space of 1 to 1000 μm therebetween, and the peripheral regions are sealed with a sealing agent 5 except for the injection port. Then an ion conductive material 6 is injected according to the above method, thereby obtaining a smart window.

In arranging the transparent electrically conductive plates 1a and 1b in a facing relation to each other, a spacer is employed for confirming regular spaces therebetween. There is no limitation to the spacer employed, and a bead made of glass or a polymer material or a glass sheet may be used. The spacers may be positioned by inserting into the space between the facing electrically conductive plates, or by forming protrusions constructed with an insulating material such as a resin on the electrodes of the electrically conductive plates.

The ion conductive material 6 may be placed, for example by injecting a precursor of the aforementioned solid ion conductive material into a space between the facing electrically conductive plates, and then curing the same. The curing method is not particularly limited, and curing by irradiation, by heat, or by mixing a reactive liquid which is cured with the lapse of time immediately before the injection, injecting the mixture immediately, and curing the mixture, may be employed.

In the case of the smart window having the structure as shown in FIG. 2, an intermediate layer 7 is formed on a transparent substrate 1a, and then the same procedures as for the structure as shown in FIG. 1 are followed, thereby obtaining a smart window. In the case of the smart window having the structure as shown in FIG. 3, an organic ultraviolet absorbing layer 3 is formed on a transparent substrate 1a, an overcoating layer 8 is formed thereon, and then the same procedures as for the structure as shown in FIG. 1 are followed, thereby obtaining a smart window. In the case of the smart window having the structure as shown in FIG. 4, an intermediate layer 7, an organic ultraviolet absorbing layer 3, an overcoating layer 8 are formed in order on a transparent substrate 1a, and then the same procedures as for the structure as shown in FIG. 1 are followed, thereby obtaining a smart window.

Since the electrochromic device of the present invention is provided with the ultraviolet absorbing layer containing the organic ultraviolet absorber between the transparent substrate and the transparent electrode, it has durability and ultraviolet resistance for enduring the usage in outdoors, as well as high electrical conductivity, and can be prepared at low cost. Particularly, it is capable of cutting the ultraviolet rays with the wave length of 400 nm or less quite effectively by suitably selecting the ultraviolet absorbing layer employed. Further, the transparent electrode can easily be formed, and the electrochromic device such a smart window can be protected from ultraviolet rays by adopting the structure wherein an overcoating layer is provided between the ultraviolet absorbing layer and the transparent electrode. Still further, the stability of the ultraviolet absorbing layer in forming the transparent electrode can be maintained by employing, as an ultraviolet absorbing layer, a layer obtained by chemically bonding the organic ultraviolet absorbing material and the basic material.

Therefore, the electrochromic device of the present invention may advantageously be utilized as a smart window or an electrochromic display, and in particular as those used outdoors. Specifically, the electrochromic device of the present invention may be utilized as an indoor window, a window facing outdoors, a skylight, a material of a window for a solar house, a partition, and the like.

EXAMPLES OF THE INVENTION

The present invention is now explained with reference to Examples which are merely illustrative and are not intended for limiting the invention.

Example 1

Preparation of Organic Ultraviolet Absorbing Layer

To a mixture of 1.89 g of an acrylic resin solution manufactured by TOAGOSEI CHEMICAL INDUSTRY CO., LTD. under the trade name of S-4030 and 0.63 g of a melamine resin solution manufactured by SANWA CHEMICAL CO., LTD. under the trade name of MX-470, were added 9.18 g of 2-propanol, and further 0.80 g of octyl 3-(5-chloro-2H-benzotrriazole-2-yl)-5-(1,1-dimethylethyl)-4-hydroxy-benzene propanate manufactured by CIBA GEIGY INC. under the trade name of TINUVIN 109, to give a coating solution. Using a 10 mil applicator, the coating solution was coated on a glass substrate by a doctor blade method. The resulting coating film on the glass substrate was dried on a hot plate at 60° C. for 30 minutes and cured by heating at 170° C. for two hours in a heating oven for forming an organic ultraviolet absorbing layer made of an acrylic melamine resin with a thickness of 70 μm.

Preparation of Transparent Electrically Conductive Plate Having Organic Ultraviolet Absorbing Layer On the obtained organic ultraviolet absorbing layer was spray-coated a silicone resin coating liquid manufactured by NIPPON UNICAR COMPANY LTD. under the trade name of APZ-6615 diluted twice the original volume with ethanol. After drying the solvent, the resulting layer was cured by heating at 100° C. for 20 minutes for forming an overcoating layer of a silicone resin of about 6.5 μm thick on the organic ultraviolet absorbing layer.

Figure 6:
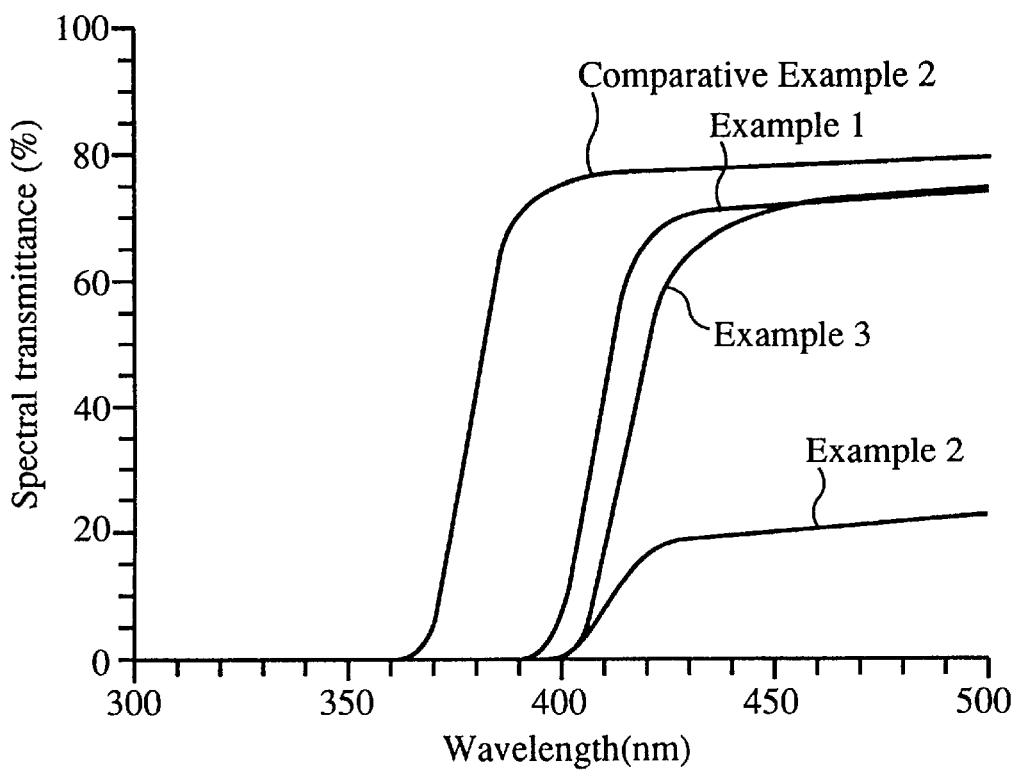
FIG. 6 is a graph showing spectral transmittance of each of the transparent electrically conductive plates prepared in Examples 1 to 3 and Comparative Example 2.

Then, sputtering of ITO was performed thereon at substrate temperature of 200° C. for forming a transparent electrode having a film thickness of about 3900 Å with a surface resistivity of 8.2 $\Omega/cm^2$, thereby obtaining a transparent electrically conductive plate having the organic ultraviolet absorbing layer, the overcoating layer, and the transparent electrode formed in order on the transparent glass substrate. The spectral transmittance of the transparent electrically conductive plate measured by a spectrophotometer is shown in FIG. 6.

Preparation of Electrochromic Electrode

On an ITO glass of 10 cm×10 cm in size, $WO_3$ was vapor-deposited to have a thickness of about 5000 Å at a rate of 20 to 30 Å/second for forming an electrochromic layer to prepare an electrochromic electrode.

Preparation of Counterelectrode

On the transparent electrically conductive plate of 10 cm×10 cm in size having the organic ultraviolet absorbing layer, active carbon fibers having a surface area of 1500 $m^2/g$ manufactured by GUNEI CHEMICAL INDUSTRY CO., LTD., were bonded in the form of grid using an electrically conductive adhesive manufactured by TOKURIKI KAGAKU CO., LTD. under the trade name of SILVEST P-255. The shape of the grid of the active carbon fibers was of a grid line interval of 2 cm and a grid line width of 0.8 mm. The amount of the active carbon fibers was 0.85 mg/cm. Subsequently, a polyester film was bonded on the active carbon fibers for providing an insulating layer to prepare a counterelectrode.

Preparation of Smart Window

The electrochromic electrode was placed facing the counterelectrode with a gap of of 1 mm therebetween, and the peripheral region was sealed with an epoxy resin with a width of 5 mm. The inner space of the assembly was charged in vacuum with a propylene carbonate solution of $LiClO_4$ (1M/liter) as an electrolyte, and the injection port was sealed with an epoxy resin. Electric wires were connected to the electrochromic electrode and the counterelectrode for preparing a smart window. The properties of the smart window thus prepared were evaluated by the following tests.

Coloring and Bleaching Test

An electrical voltage of 1V was applied for 120 seconds across the electrochromic electrode as a negative terminal and the counterelectrode as a positive terminal. It was seen that the resulting assembly was colored uniformly in blue, with the optical density on coloration being 1.08. Subsequently, an electrical voltage of 1V was applied for 60 seconds across the electrochromic electrode as a positive terminal and the counterelectrode as a negative terminal. It was seen that coloration disappeared quickly, with the optical density at the time of color extinction being 0.20. Thus the optical density difference between coloration and bleaching was 0.88.

Cyclic Test Under Irradiation of Ultraviolet Ray

The coloring and bleaching test was performed for 1200 cycles in Suntest (trade name) manufactured by HERAEUS INDUSTRIE TECHNIK. It was seen that cyclic characteristics were highly stable without any remnant coloring, lowering in response or lowering in the optical density difference.

Example 2

Preparation of Organic Ultraviolet Absorbing Layer

To 11.1 ml of silicone varnish coating manufactured by OKITSUMO CO. under the trade name of "XO-7931-CLEAR" was added 5 g of 3-(5-chloro-2H-benzotriazole-2-yl)-5-(1,1-dimethylethyl)-4-hydroxy-N-(3-(triethoxysilyl)propyl)benzene propanamide. To the resulting mass were added 1 ml of water, 0.1 ml of acetic acid and 10 $\mu$l of di-n-butyltin dilaurate. The resulting mass was allowed to stand at 60° C. for 24 hours, and then spray-coated on a glass substrate. The resulting coating film on a glass substrate was dried on a hot plate at 60° C. for 15 minutes and cured by heating at 200° C. for 1 hour in a heating oven for forming an organic ultraviolet absorbing layer of about 15 $\mu$m thick. No components of the ultraviolet absorbing layer were seen to be eluted even in chloroform.

Preparation of Transparent Electrically Conductive Plate Having Organic Ultraviolet Absorbing Layer On the obtained organic ultraviolet absorbing layer, sputtering of ITO was performed at substrate temperature of 250° C. for forming a transparent electrode having a film thickness of 3300 Å with a surface resistivity of 7.5 $\Omega/cm^2$, thereby obtaining a transparent electrically conductive plate having the organic ultraviolet absorbing layer and the transparent electrode formed in order on the transparent glass substrate. The spectral transmittance of the transparent electrically conductive plate is shown in FIG. 6.

Preparation of Electrochromic Electrode

On an ITO glass of 10 cm×10 cm in size, $WO_3$ was vapor-deposited in the same manner as in Example 1 for forming an electrochromic layer to prepare an electrochromic electrode.

Preparation of Counterelectrode

On the transparent electrically conductive plate of 10 cm×10 cm in size having the organic ultraviolet absorbing layer, an active carbon fibers were placed in the same manner as in Example 1 for preparing a counterelectrode.

Preparation of Precursor of Solid Ion Conductive Material 1 g of methoxypolyethylene glycol #230 methacrylate manufactured by SHINNAKAMURA CHEMICAL INDUSTRIAL CO., LTD., under the trade name of M-40G, 0.02 g of polyethylene glycol #400 dimethacrylate, manufactured by SHINNAKAMURA CHEMICAL INDUSTRIAL CO., LTD., under the trade name of 9 G, and 20 mg of photopolymerization initiator manufactured by CIBA GEIGY INC. under the trade name of DAROCUR 1173 were dissolved in 4 g of 1M-$LiClO_4$/$\gamma$-butylolactone solution to obtain a precursor of solid ion conductive material.

Preparation of Smart Window

The electrochromic electrode was placed facing the counterelectrode with glass beads having a diameter of 200 $\mu$m therebetween, and the peripheral region was sealed with an epoxy resin with a width of 5 mm. The inner space of the assembly was charged in vacuum with the precursor of solid ion conductive material, and the injection port was sealed with an epoxy resin. By irradiating the light of a high-pressure mercury lamp, the precursor of solid ion conductive material was cured to be a solid ion conductive material. Electric wires were connected to the electrochromic electrode and the counterelectrode for preparing a smart window. The properties of the smart window thus prepared were evaluated by the following tests.

Coloring and Bleaching Test

An electrical voltage of 1V was applied for 120 seconds across the electrochromic electrode as a negative terminal and the counterelectrode as a positive terminal. It was seen that the resulting assembly was colored uniformly in blue, with the optical density on coloration being 1.15. Subsequently, an electrical voltage of 1V was applied for 60 seconds across the electrochromic electrode as a positive terminal and the counterelectrode as a negative terminal. It was seen that coloration disappeared quickly, with the optical density at the time of color extinction being 0.25. Thus the optical density difference between coloration and bleaching was 0.90.

Cyclic Test Under Irradiation of Ultraviolet Ray

The coloring and bleaching test was performed for 1200 cycles in Suntest (trade name) manufactured by HERAEUS INDUSTRIE TECHNIK. It was seen that cyclic characteristics were highly stable without any remnant coloring, lowering in response or lowering in the optical density difference.

Example 3

Preparation of Intermediate Layer

An ultra-fine ZnO particle-suspended coating manufactured by RESINO COLOR INDUSTRY CO., LTD. under the trade name of UV-S-400 was applied by dip coating on a glass substrate and cured by heating at 200° C. for 20 minutes for forming a far ultraviolet absorbing layer of about 2 82 m in thickness. Then, a methylene chloride solution of polyether sulfone manufactured by ICI LTD. under the trade name of VICTREX PES 4100P was spin-coated thereon for forming a polymer layer of about 2 $\mu$m in thickness to obtain an intermediate layer consisting of the far ultraviolet absorbing layer and the polymer layer.

Preparation of Organic Ultraviolet Absorbing Layer

On the obtained intermediate layer, an organic ultraviolet absorbing layer of about 15 $\mu$m in thickness was formed in the same manner as in Example 2.

Preparation of Overcoating Layer

On the obtained organic ultraviolet absorbing layer, polyimide varnish manufactured by NISSAN CHEMICAL INDUSTRIES, LTD. under the trade name of RN812 was spin-coated. The solvent is then dried off at 60° C. on a hot plate and the resulting product was cured by heating in an oven at 200° C. for 30 minutes to obtain an overcoating layer of about 2 $\mu$m in thickness.

Preparation of Transparent Electrically Conductive Plate Having Organic Ultraviolet Absorbing Layer On the obtained overcoating layer, sputtering of ITO was performed at substrate temperature of not more than 250° C. for forming a transparent electrode having a film thickness of about 2050 Å with a surface resistivity of 9.5 $\Omega/cm^2$, thereby obtaining a transparent electrically conductive plate having the intermediate layer, the organic ultraviolet absorbing layer containing an organic ultraviolet absorber, the overcoating layer, and the transparent electrode formed in order on the transparent glass substrate. The spectral transmittance of the transparent electrically conductive plate is shown in FIG. 6.

Preparation of Electrochromic Electrode

Using the transparent electrically conductive plate of 10 cm×10 cm in size having the organic ultraviolet absorbing layer, electrolytic polymerization was performed in a 0.5N perchloric acid solution containing 5 mol/liter of aniline hydrochloride with an electric current density of 500 $\mu A/cm^2$, for forming an electrochromic layer of a polyaniline film of 70 $cm^2$ in the polymerized area and 3000 Å in thickness to obtain an electrochromic electrode.

Preparation of Counterelectrode

On an ITO glass of 10 cm×10 cm in size, powders of polypyrrole having a surface area of 73 $m^2/g$ obtained by electrolytic polymerization were bonded in the form of lateral stripes, using an electrically conductive adhesive manufactured by TOKURIKI KAGAKU CO., LTD. under the trade name of SILVEST P-255. The line interval of the stripes was 1 cm, and the line width of the stripes was 0.5 mm. The amount of the polypyrrole powders was 0.65 mg/cm. Subsequently, a polyester film was bonded on the polypyrrole lines for providing an insulating layer to prepare a counterelectrode.

Preparation of Precursor of Solid Ion Conductive Material 10 g of methoxytetraethylene glycol methacrylate, 0.1 g of tetraethylene glycol dimethacrylate, 40 g of γ-butylolactone and 4 g of $LiClO_4$ (lithium pechlorate) were mixed. In the darkness, 0.2 g of photopolymerization initiator manufactured by CIBA GEIGY INC. under the trade name of DAROCURE 1173 were added to the mass.

Preparation of Smart Window

The electrochromic electrode was placed facing the counterelectrode with glass beads having a diameter of 200 $\mu$m therebetween, and the peripheral region was sealed with an epoxy resin with a width of 5 mm. The inner space of the assembly was charged in vacuum with the precursor of solid ion conductive material, and the injection port was sealed with an epoxy resin. By irradiating the light of a high-pressure mercury lamp for 20 seconds, the precursor of solid ion conductive material was cured to be a solid ion conductive material, Electric wires were connected to the electrochromic electrode and the counterelectrode for preparing a smart window. The properties of the smart window thus prepared were evaluated by the following tests.

Coloring and Bleaching Test

An electrical voltage of 1V was applied for 120 seconds across the electrochromic electrode as a negative terminal and the counterelectrode as a positive terminal. It was seen that the resulting assembly was colored uniformly in blue, with the optical density on coloration being 0.65. Subsequently, an electrical voltage of 1V was applied for 60 seconds across the electrochromic electrode as a positive terminal and the counterelectrode as a negative terminal. It was seen that coloration disappeared quickly, with the optical density at the time of color extinction being 0.20. Thus the optical density difference between coloration and bleaching was 0.45.

Cyclic Test Under Irradiation of Ultraviolet Ray

The coloring and bleaching test was performed for 1200 cycles in Suntest (trade name) manufactured by HERAEUS INDUSTRIE TECHNIK. It was seen that cyclic characteristics were highly stable without any remnant coloring, lowering in response or lowering in the optical density difference.

Comparative Example 1

Preparation of Electrochromic Electrode

On an ITO glass of 10 cm×10 cm in size, $WO_3$ was vapor-deposited in the same manner as in Example 1 for forming an electrochromic layer to prepare an electrochromic electrode.

Preparation of Counterelectrode

On an ITO glass of 10 cm×10 cm in size which was not provided with an organic ultraviolet absorbing layer and an overcoating layer, an active carbon fibers were placed in the same manner as in Example 1 for preparing a counterelectrode.

Preparation of Smart Window

The electrochromic electrode was placed facing the counterelectrode with a gap of of 1 mm therebetween, and the peripheral region was sealed with an epoxy resin with a width of 5 mm. The inner space of the assembly was charged in vacuum with a propylene carbonate solution of $LiClO_4$ (1M/liter) as an electrolyte, and the injection port was sealed with an epoxy resin. Electric wires were connected to the electrochromic electrode and the counterelectrode for preparing a smart window. The properties of the smart window thus prepared were evaluated by the following tests.

Coloring and Bleaching Test

An electrical voltage of 1V was applied for 120 seconds across the electrochromic electrode as a negative terminal and the counterelectrode as a positive terminal. It was seen that the resulting assembly was colored uniformly in blue, with the optical density on coloration being 1.08. Subsequently, an electrical voltage of 1V was applied for 60 seconds across the electrochromic electrode as a positive terminal and the counterelectrode as a negative terminal. It was seen that coloration disappeared quickly, with the optical density at the time of color extinction being 0.20. Thus the optical density difference between coloration and bleaching was 0.88.

Cyclic Test Under Irradiation of Ultraviolet Ray

The coloring and bleaching test was performed for 1200 cycles in Suntest (trade name) manufactured by HERAEUS INDUSTRIE TECHNIK. Remnant coloration and the lowering in the response were noticed. The optical density difference was lowered to 0.25.

Comparative Example 2

Preparation of Inorganic Ultraviolet Absorbing Layer

An ultra-fine ZnO particle-suspended coating manufactured by RESINO COLOR INDUSTRY CO., LTD. under the trade name of UV-S-400 was applied by dip coating on a glass substrate and cured by heating at 200° C. for 20 minutes for forming an inorganic ultraviolet absorbing layer of about 2 $\mu$m in thickness.

Preparation of Transparent Electrically Conductive Plate Having Ultraviolet Absorbing Layer On the obtained inorganic ultraviolet absorbing layer, sputtering of ITO was performed at substrate temperature of 250° C. for forming a transparent electrode having a film thickness of about 2050 Å with a surface resistivity of 9.5 $\Omega/cm^2$, thereby obtaining a transparent electrically conductive plate having the inorganic ultraviolet absorbing layer and the transparent electrode formed in order on the transparent glass substrate. The spectral transmittance of the transparent electrically conductive plate is shown in FIG. 6.

Preparation of Electrochromic Electrode

On an ITO glass of 10 cm×10 cm in size, $WO_3$ was vapor-deposited in the same manner as in Example 1 for forming an electrochromic layer to prepare an electrochromic electrode.

Preparation of Counterelectrode

On the transparent electrically conductive plate of 10 cm×10 cm in size having the inorganic ultraviolet absorbing layer, an active carbon fibers were placed in the same manner as in Example 1 for preparing a counterelectrode.

Preparation of Smart Window

Using the electrochromic electrode and the counterelectrode, a smart window was prepared by charging the solid ion conductive material in the space in the same manner as in Example 3, and connecting lead wires to the electrochromic electrode and the counterelectrode. The properties of the smart window thus prepared were evaluated by the following tests.

Coloring and Bleaching Test

An electrical voltage of 1V was applied for 120 seconds across the electrochromic electrode as a negative terminal and the counterelectrode as a positive terminal. It was seen that the resulting assembly was colored uniformly in blue, with the optical density on coloration being 1.15. Subsequently, an electrical voltage of 1V was applied for 60 seconds across the electrochromic electrode as a positive terminal and the counterelectrode as a negative terminal. It was seen that coloration disappeared quickly, with the optical density at the time of color extinction being 0.25. Thus the optical density difference between coloration and bleaching was 0.90.

Cyclic Test Under Irradiation of Ultraviolet Ray

The coloring and bleaching test was performed for 1200 cycles in Suntest (trade name) manufactured by HERAEUS INDUSTRIE TECHNIK. Remnant coloration and the lowering in the response were noticed. The optical density difference was lowered to 0.65.

Although the present invention has been described with reference to the preferred examples, it should be understood that various modification and variation can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. An electrochromic device comprising:
   a pair of electrically conductive counter plates;
   an ion conductive material placed between said electrically conductive counter plates;
   a layer containing an electrochromic material provided in at least one of locations between said ion conductive material and the electrically conductive counter plates;
   at least one of said electrically conductive counter plates being a transparent electrically conductive plate comprising a transparent substrate and a transparent electrode disposed inside the transparent substrate; and
   at least one of said transparent electrically conductive plates comprising an ultraviolet absorbing layer between said transparent substrate and said transparent electrode, said ultraviolet absorber layer comprising a resin material and an organic ultraviolet absorber chemically bonded to said resin material.

2. The electrochromic device as claimed in claim 1 wherein said transparent electrode is made of a material selected from the group consisting of ITO($In_2O_3$—$SnO_2$), tin oxide, zinc oxide, vanadium oxide, and mixtures thereof.

3. The electrochromic device as claimed in claim 1 wherein said transparent electrode is provided with an opaque electrode active material selected from the group consisting of copper, silver, gold, platinum, iron, tungsten, titanium, lithium, polyaniline, polythiophene, polypyrrole, phthalocyanine, active carbon fibers, graphite, $V_2O_5$, $WO_3$, $MnO_2$, NiO, $Ir_2O_3$, and mixtures thereof.

4. The electrochromic device as claimed in claim 1 wherein said ion conductive material is selected from the group consisting of a liquid ion conductive material wherein a support electrolyte is dissolved in a solvent, a gelated liquid ion conductive material wherein a polymer and/or a gelatinizer is contained in said liquid ion conductive material, and solid ion conductive material.

5. The electrochromic device as claimed in claim 4 wherein said solid ion conductive material is a polymeric solid electrolyte.

6. The electrochromic device as claimed in claim 5 wherein said polymeric solid electrolyte is selected from the group consisting of a solidified body of a composition A comprising urethane acrylate represented by the formula (1), an organic polar solvent, and a support electrolyte:

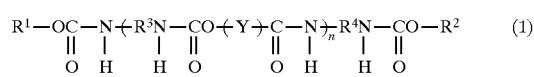

wherein $R^1$ and $R^2$ are the same or different groups, and stand for

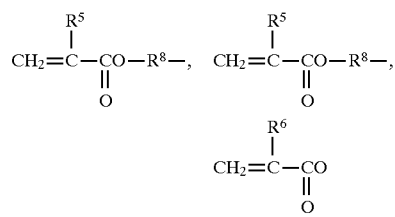

or

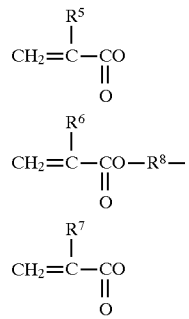

wherein $R^5$ to $R^7$ are the same or different groups and stand for a hydrogen atom or an alkyl group having 1 to 3 carbon atoms, $R^8$ stands for a divalent, trivalent, or tetravalent organic residue having 1 to 20 carbon atoms, $R^3$ and $R^4$ are the same or different groups and stand for divalent hydrocarbon residue having 1 to 20 carbon atoms, Y stands for a polyether unit, a polyester unit, a polycarbonate unit, or a combined unit thereof, and n stands for an integer of 1 to 100, and a solidified body of a composition B comprising a monofunctional acryloyl-modified polyalkylene oxide represented by the formula (2), a polyfunctional acryloyl-modified polyalkylene oxide, an organic polar solvent, and a support electrolyte:

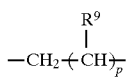

wherein $R^9$ stands for an alkyl group having 1 to 3 carbon atoms or a hydrogen atom, p stands for an integer of 0 to 6, when $2 \leq p$, $R^9$ may be the same or different.

7. The electrochromic device as claimed in claim 6 wherein said organic polar solvent is selected from the group consisting of methanol, ethanol, propylene carbonate, ethylene carbonate, dimethylsulfoxide, dimethoxyethane, acetonitrile, γ-butyrolactone, sulfolane, 1,3-dioxane, N,N-dimethylformamide, 1,2-dimethoxyethane, tetrahydrofurane, and mixtures thereof.

8. The electrochromic device as claimed in claim 6 wherein said support electrolyte is selected from the group consisting of $LiClO_4$, LISCN, $LiBF_4$, $LiAsF_6$, $LiCF_3SO_3$, $LiPF_6$, LiI, NaI, NaSCN, $NaClO_4$, $NaBF_4$, $NaAsF_6$, KSCN, KCl, $(CH_3)_4NBF_4$, $(C_2H_5)_4NBF_4$, $(n-C_4H_9)_4NBF_4$, $(C_2H_5)_4NBr$, $(C_2H_5)_4NClO_4$, $(n-C_4H_9)_4NClO_4$, sulfuric acid hydrochloric acid, phospholic acids, sulfonic acids, carboxylic acids, sodium hydroxide, potassium hydroxide, and lithium hydroxide.

9. The electrochromic device as claimed in claim 6 wherein a mixing ratio of said organic polar solvent in the composition A is 100 to 1200 parts by weight based on 100 parts by weight of said urethane acrylate represented by the formula (1), and a mixing ratio of said support electrolyte in the composition A is 0.1 to 30% by weight of a total weight of said organic polar solvent.

10. The electrochromic device as claimed in claim 6 wherein the composition A further comprising an optional component selected from the group consisting of a crosslinking agent, a photopolymerization initiator, and a thermopolymerization initiator.

11. The electrochromic device as claimed in claim 6 wherein said monofunctional acryloyl-modified polyalkylene oxide represented by the formula (2) is selected from the group consisting of methoxypolyethylene glycol methacrylate, methoxypolypropylene glycol methacrylate, ethoxypolyethylene glycol methacrylate, ethoxypolypropylene glycol methacrylate, methoxypolyethylene glycol acrylate, methoxypolypropylene glycol acrylate, ethoxypolyethylene glycol acrylate, ethoxypolypropylene glycol acrylate, methoxypoly(ethylene/propylene) glycol methacrylate having 1 to 50 oxyethylene polymer units and 1 to 50 oxypropylene polymer units, ethoxypoly(ethylene/propylene) glycol methacrylate having 1 to 50 oxyethylene polymer units and 1 to 50 oxypropylene polymer units, methoxypoly(ethylene//propylene) glycol acrylate having 1 to 50 oxyethylene polymer units and 1 to 50 oxypropylene polymer units, and ethoxypoly(ethylene/propylene) glycol acrylate having 1 to 50 oxyethylene polymer units and 1 to 50 oxypropylene polymer units, and mixtures thereof.

12. The electrochromic device as claimed in claim 6 wherein said polyfunctional acryloyl-modified polyalkylene oxide is selected from the group consisting of polyethylene glycol dimethacrylate, polypropylene glycol dimethacrylate, polyethylene glycol diacrylate, polypropylene glycol diacrylate, poly(ethylene/propylene) glycol dimethacrylate having 1 to 50 oxyethylene polymer units and 1 to 50 oxypropylene polymer units, poly(ethylene/propylene) glycol diacrylate having 1 to 50 oxyethylene polymer units and 1 to 50 oxypropylene polymer units, trimethylolpropane tri(polyethylene glycol acrylate), trimethylolpropane tri(polyethylene glycol methacrylate), trimethylolpropane tri(polypropylene glycol acrylate), trimethylolpropane tri (polypropylene glycol methacrylate), tetramethylolmethane tetra(polyethylene glycol acrylate), tetramethylolmethane tetra(polyethylene glycol methacrylate), tetramethylolmethane tetra(polypropylene glycol acrylate), tetramethylolmethane tetra(polypropylene glycol methacrylate), 2,2-bis (4-(acryloyloxypolyethoxy) phenyl)propane, 2,2-bis(4-(methacryloyloxypolyethoxy) phenyl)propane, 2,2-bis(4-(acryloyloxypolyisopropoxy) phenyl) propane, 2,2-bis(4-(methacryloyloxypolyisopropoxy)phenyl)propane, trimethylolpropane tri(poly(ethylene/propylene)glycol acrylate) having 1 to 50 oxyethylene polymer units and 1 to 50 oxypropylene polymer units, trimethylolpropane tri(poly(ethylene/propylene) glycol methacrylate) having 1 to 50 oxyethylene polymer units and 1 to 50 oxypropylene polymer units, tetramethylolmethane tetra(poly(ethylene/propylene) glycol acrylate) having 1 to 50 oxyethylene polymer units and 1 to 50 oxypropylene polymer units, tetramethylolmethane tetra(poly(ethylene/propylene) glycol methacrylate) having 1 to 50 oxyethylene polymer units and 1 to 50 oxypropylene polymer units, and mixtures thereof.

13. The electrochromic device as claimed in claim 6 wherein in the composition B, a mixing ratio of the polyfunctional acryloyl-modified polyalkylene oxide to the monofunctional acryloyl-modified polyalkylene oxide is 0.001 to 1:1 in weight ratio, a mixing ratio of the organic polar solvent is 50 to 800% by weight of a total weight of the monofunctional acryloyl-modified polyalkylene oxide and the polyfunctional acryloyl-modified polyalkylene oxide, and a mixing ratio of the supporting electrolyte is 1 to 30% by weight of a total weight of the monofunctional acryloyl-modified polyalkylene oxide, the polyfunctional acryloyl-modified polyalkylene oxide, and the organic polar solvent.

14. The electrochromic device as claimed in claim 6 wherein said composition B further comprising a polymerization initiator selected from the group consisting of a photopolymerization initiator and a thermopolymerization initiator.

15. The electrochromic device as claimed in claim 5 wherein said polymeric solid electrolyte is obtained by solidifying a composition containing a monofunctional acryloyl-modified polyalkylene oxide, a polyfunctional acryloyl-modified polyalkylene oxide, an organic polar solvent, and a support electrolyte.

16. The electrochromic device as claimed in claim 15 wherein said monofunctional acryloyl-modified polyalkylene oxide is a compound represented by the formula (2)

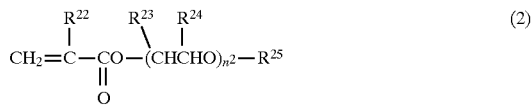

wherein $R^{22}$, $R^{23}$, $R^{24}$ and $R^{25}$ are the same or different groups and stand for a hydrogen atom or an alkyl group having 1 to 5 carbon atoms, and $n^2$ stands for an integer satisfying $1 \leq n^2 \leq 100$, and said polyfunctional acryloyl-modified polyalkylene oxide is selected from the group consisting of a compound represented by the formula (A), a compound represented by the formula (B) and mixtures thereof:

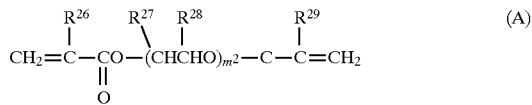

wherein $R^{26}$, $R^{27}$, $R^{28}$, and $R^{29}$ are the same or different groups and stand for a hydrogen atom or an alkyl group having 1 to 5 carbon atoms, and $m^2$ stands for an integer satisfying $1 \leq m^2 \leq 100$,

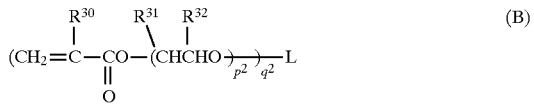

wherein $R^{30}$, $R^{31}$ and $R^{32}$, are the same or different groups and stand for a hydrogen atom or an alkyl group having 1 to 5 carbon atoms, $p^2$ stands for an integer satisfying $1 \leq p^2 \leq 100$, $q^2$ stands for an integer satisfying $2 \leq q^2 \leq 4$, and L stands for a coupling hydrocarbon group of the valency of $q^2$ having 1 to 30 carbon atoms.

17. The electrochromic device as claimed in claim 16 wherein said coupling hydrocarbon group represented by L in the formula (B) is selected from the group consisting of an alkylene group, an arylene group, an arylalkylene group, an alkylarylene group, an alkyltriyl group, an aryltriyl group, an arylalkyltriyl group, an alkylaryltriyl group, an alkyltetrayl group, an aryltetrayl group, an arylalkyltetrayl group, and an alkylaryltetrayl group.

18. The electrochromic device as claimed in claim 15 wherein a mixing ratio of said polyfunctional acryloyl-modified polyalkylene oxide to said monofunctional acryloyl-modified polyalkylene oxide is 0.001 to 1:1 in weight ratio.

19. The electrochromic device as claimed in claim 15 wherein said organic polar solvent is selected from the group consisting of propylene carbonate, ethylene carbonate, dimethylsulfoxide, dimethoxyethane, acetonitrile, γ-butyrolactone, sulfolane, 1,3-dioxane, N,N-dimethylformamide, 1,2-dimethoxyethane, tetrahydrofuran and mixtures thereof.

20. The electrochromic device as claimed in claim 15 wherein said support electrolyte is selected from the group consisting of $LiClO_4$, LiSCN, $LiBF_4$, $LiAsF_6$, $LiCF_3SO_3$, $LiPF_6$, LiI, NaI, NaSCN, $NaClO_4$, $NaBF_4$, $NaAsF_6$, KSCN KCl, $(CH_3)_4NBF_4$, $(C_2H_5)_4NBF_4$, $(n-C_4H_9)_4NBF_4$, $(C_2H_5)_4NBr$ $(C_2H_5)_4NClO_4$, $(n-C_4H_9)_4NClO_4$ and mixtures thereof.

21. The electrochromic device as claimed in claim 15 wherein said composition further comprises a polymerization initiator selected from the group consisting of a photopolymerization initiator and a thermopolymerization initiator.

22. The electrochromic device as claimed in claim 15 wherein a mixing ratio of said organic polar solvent is 50 to 800% by weight of the total weight of the monofunctional acryloyl-modified polyalkylene oxide and the polyfunctional acryloyl-modified polyalkylene oxide together.

23. The electrochromic device as claimed in claim 15 wherein a mixing ratio of said support electrolyte is 1 to 30% by weight of the total weight of the monofunctional acryloyl-modified polyalkylene oxide, the polyfunctional acryloyl-modified polyalkylene oxide, and the organic polar solvent together.

24. The electrochromic device as claimed in claim 1 wherein said electrochromic material is selected from the group consisting of $Mo_2O_3$, $Ir_2O_3$, NiO, $V_2O_5$, $WO_3$, viologen, polythiophene, polyaniline, polypyrrole, metalophthalocyanine, and mixtures thereof.

25. The electrochromic device as claimed in claim 1 wherein said organic ultraviolet absorber is selected from the group consisting of 2-(2'-hydroxy-5'-methylphenyl)benzotriazole, 2-(2'-hydroxy-3',5'-bis(α,α-dimethylbenzyl)phenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, octyl 3-(5-chloro-2H-benzotriazole-2-yl)-5-(1,1-dimethylethyl)-4-hydroxy-benzenepropanoate, 2,4-dihydroxybenzophenone, 2-hydroxy-4-methoxybenzophenone, 2-hydroxy-4-methoxybenzophenone-5-sulfonic acid, 2-hydroxy-4-n-octoxybenzophenone, 2,2'-dihydroxy-4,4'-dimethoxybenzophenone, 2,2',4,4'-tetrahydroxybenzophenone, 2-hydroxy-4-methoxy-2'-carboxybenzophenone, and mixtures thereof.

26. The electrochromic device as claimed in claim 1 wherein said resin material is selected from the group consisting of polyester resin, silicone resin, acrylic resin, melamine resin, phenol resin, polycarbonate resin, epoxy resin, polystyrene resin, polyether resin, polyamide resin, polyimide resin, fluoro resin, and mixtures thereof.

27. The electrochromic device as claimed in claim 1 wherein said layer wherein said organic ultraviolet absorber is chemically bonded to said resin material is obtained by reacting the organic ultraviolet absorber having a group which reacts with a functional group in a material selected from the group consisting of the resin material, a precursor of the resin material, and mixtures thereof, with a material selected from the group consisting of the resin material, a precursor of the resin material, and mixtures thereof.

28. The electrochromic device as claimed in claim 27 wherein said organic ultraviolet absorber is selected from the group consisting of 3-(5-methyl-2H-benzotriazole-2-yl)-5-methyl-4-hydroxy-N-(2-(trimethoxysilyl)ethyl)-benzene propanamide, 3-(5-ethyl-2H-benzotriazole-2-yl)-4-hydroxy-N-(2-(1,1,3,3-tetramethyldisiloxy)ethyl)-benzene propanamide, 3-(2H-benzotriazole-2-yl)-4-hydroxybenzene ethyl-N-(3-trimethoxysilyl)propyl)carbamate, 3-(5-chloro-2H-benzotriazole-2-yl)-4-hydroxybenzene propyl-N-(2-nonaphenyltetrasiloxy)ethyl)carbamate, 3-(5-chloro-2H-benzotriazole-2-yl)-5-(1,1-dimethylethyl)-4-hydroxy-N-(3-(triethoxysilyl)propyl)-benzene propanamide, 3-(5-chloro-2H-benzotriazole-2-yl)-5-(1,1-dimethylethyl)-4-hydroxy-N-(3-(triethoxysilyl)propyl)-benzene propanamide, 3-(5-chloro-2H-benzotriazole-2-yl)-5-(1,1-dimethylethyl)-4-hydroxy-N-(3-henicosamethyldecasiloxy) propyl-benzene propanamide, 3-(2H-benzotriazole-2-yl)-4hydroxy-N-(2-(1,1-dimethyl-trimethoxydisiloxy)ethyl)-benzene propaneamide, 3-(triethoxysilyl)propyl-3-(5-chloro-2H-benzotriazole-2-yl)-5-(1,1-dimethylethyl)-4-hydroxy-benzene propanate, 3-(1,1,3,3,5,5,5-heptamethyltrisiloxy)propyl-3-(5-chloro-2H-benzotriazole-2-yl)-5-(1,1-dimethylethyl)-4-hydroxy-benzene propanate, 3-(diethoxymethylsilyl)propyl-3-(2H-benzotriazole-2-yl)-5-(1,1-dimethylethyl)-4-hydroxy-benzene propanate, and mixtures thereof.

29. The electrochromic device as claimed in claim 27 wherein said resin material is selected from the group consisting of polyester resin, silicone resin, acrylic resin, melamine resin, phenol resin, polycarbonate resin, epoxy resin, polystyrene resin, polyether resin, polyamide resin, polyimide resin, fluoro resin, and mixtures thereof.

30. The electrochromic device as claimed in claim 27 wherein said precursor of the resin material is selected from the group consisting of methacrylate monomer, alkoxysilane monomer, acrylic oligomer, silicone oligomer, and mixtures thereof.

31. The electrochromic device as claimed in claim 27 wherein said organic ultraviolet absorber is a compound represented by the formula

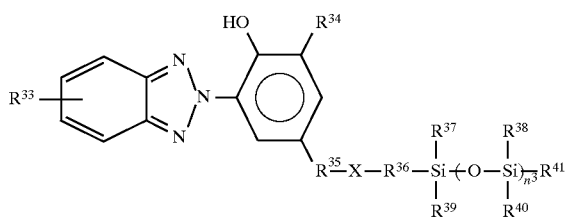

wherein $R^{33}$ stands for a hydrogen atom, halogen atom or an alkyl group having 1 to 10 carbon atoms, $R^{34}$ stands for a hydrogen atom or an alkyl group having 1 to 10 carbon atoms, $R^{35}$ and $R^{36}$ are the same or different groups and stand for an alkylene group having 1 to 6 carbon atoms, $R^{37}$ to $R^{41}$ are the same or different groups and stand for an alkyl group having 1 to 10 carbon atoms, an alkoxy group having 1 to 10 carbon atoms, an aryl group having 6 to 10 carbon atoms, a hydroxyl group, or a hydrogen atom, X denotes an amido bond (CONH), an urethane bond (OCONH), or an ester bond (COO), $n^3$ stands for an integer satisfying $0 \leq n^3 \leq 20$.

32. The electrochromic device as claimed in claim 1 further comprising an overcoating layer provided between the ultraviolet absorbing layer containing the organic ultraviolet absorber and the transparent electrode.

33. The electrochromic device as claimed in claim 1 further comprising an intermediate layer provided between the transparent substrate and the ultraviolet absorbing layer containing the organic ultraviolet absorber.

34. The electrochromic device as claimed in claim 1 wherein said electrochromic device is a smart window.

35. The electrochromic device as claimed in claim 1 wherein said layer having the organic ultraviolet absorber chemically bonded to the resin material is obtained by bonding a material selected from the group consisting of the resin material and a precursor thereof with the organic ultraviolet absorber using a silane-based coupling agent.

* * * * *

UNITED STATES PATENT AND TRADEMARK OFFICE
CERTIFICATE OF CORRECTION

PATENT NO. : 5,859,722
DATED : January 12, 1999
INVENTOR(S) : Suga et al.

It is certified that error appears in the above-identified patent and that said Letters Patent is hereby corrected as shown below:

Column 20,
Lines 1-13, please delete the formula and replace with the following:
--
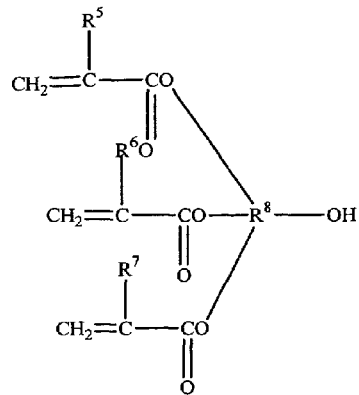
--

Column 42,
Lines 31-54, delete the formula and replace with the following:

--
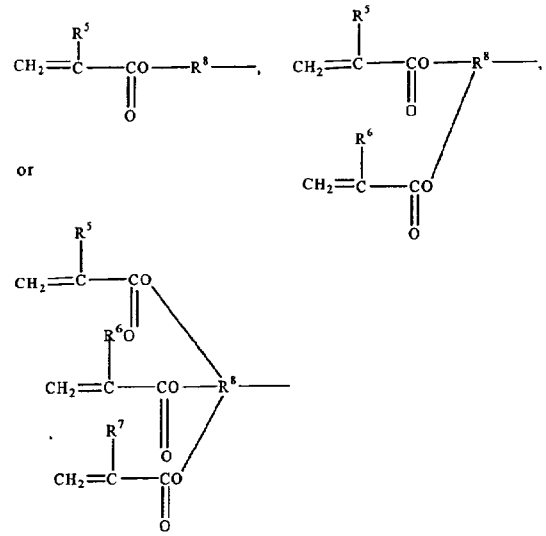
--

UNITED STATES PATENT AND TRADEMARK OFFICE
CERTIFICATE OF CORRECTION

PATENT NO.   : 5,859,722
DATED        : January 12, 1999
INVENTOR(S)  : Suga et al.

It is certified that error appears in the above-identified patent and that said Letters Patent is hereby corrected as shown below:

<u>Column 43,</u>
Line 20, after "sulfuric acid" and insert -- , --.

<u>Column 45,</u>
Line 31, change "y-butyrolactone" to -- ϒ-butyrolactone --
Line 37, change "Lil, Nal" to -- Lil, Nal --.
Line 37, after "KSCN" insert -- , --.
Lines 38 to 39, change "$(C_2H_5)_4NaBr(C_2H_5)_4NC10_4$," to
-- $(C_2H_5)_4NaBr, (C_2H_5)_4NC10_4$, --.

Signed and Sealed this

Nineteenth Day of November, 2002

*Attest:*

*Attesting Officer*

JAMES E. ROGAN
*Director of the United States Patent and Trademark Office*